United States Patent
Scherrer et al.

(10) Patent No.: US 10,718,770 B2
(45) Date of Patent: Jul. 21, 2020

(54) METHODS FOR SCREENING COMPOUNDS FOR TREATING OR PREVENTING A VIRAL INFECTION OR A VIRUS-RELATED CONDITION

(71) Applicants: ABIVAX, Paris (FR); CENTRE NATIONAL DE LA RECHERCHE SCIENTIFIQUE, Paris (FR); INSTITUT CURIE, Paris (FR); UNIVERSITE DE MONTPELLIER, Montpellier (FR)

(72) Inventors: Didier Scherrer, Castelnau Le Lez (FR); Aude Garcel, Le Cres (FR); Noelie Campos, Le Cres (FR); Jamal Tazi, Clapiers (FR); Audrey Vautrin, Castelnau Le Lez (FR); Florence Mahuteau, Saint Remy les Chevreuses (FR); Romain Najman, L'Hay-les-Roses (FR); Pauline Fornarelli, Villebon Sur Yvette (FR)

(73) Assignees: ABIVAX, Paris (FR); CENTRE NATIONAL DE LA RECHERCHE SCIENTIFIQUE, Paris (FR); INSTITUT CURIE, Paris (FR); UNIVERSITE DE MONTPELLIER, Montpellier (FR)

( * ) Notice: Subject to any disclaimer, the term of this patent is extended or adjusted under 35 U.S.C. 154(b) by 0 days.

(21) Appl. No.: 15/552,660

(22) PCT Filed: Feb. 19, 2016

(86) PCT No.: PCT/EP2016/053533
§ 371 (c)(1),
(2) Date: Aug. 22, 2017

(87) PCT Pub. No.: WO2016/135053
PCT Pub. Date: Sep. 1, 2016

(65) Prior Publication Data
US 2018/0031557 A1 Feb. 1, 2018

(30) Foreign Application Priority Data
Feb. 23, 2015 (EP) ..................... 15305276

(51) Int. Cl.
*G01N 33/53* (2006.01)
*G01N 33/569* (2006.01)

(52) U.S. Cl.
CPC ... *G01N 33/56983* (2013.01); *G01N 2333/16* (2013.01); *G01N 2469/10* (2013.01); *G01N 2500/02* (2013.01); *G01N 2500/10* (2013.01)

(58) Field of Classification Search
CPC .................................... G01N 2333/47
(Continued)

(56) References Cited

FOREIGN PATENT DOCUMENTS

| CN | 1 333 270 A | 1/2002 |
|---|---|---|
| CN | 1 333 275 A | 1/2002 |

(Continued)

OTHER PUBLICATIONS

Gonatopoulos-Pournatzis et al. Cap-binding complex (CBC), Biochem. J. 2014, vol. 457, pp. 231-242 (Year: 2014).*

(Continued)

*Primary Examiner* — Shengjun Wang
(74) *Attorney, Agent, or Firm* — Oliff PLC

(57) ABSTRACT

The present invention relates to a method for screening a compound useful for treating or preventing a viral infection or a virus-related condition in an individual, comprising at least the steps of: a) determining the ability of a candidate compound to promote the interaction between CBP20 and CBP80 in a sample, and b) selecting the candidate compound that is determined to promote said interaction at step (Continued)

a). The present invention further relates to a method for screening a compound useful for treating or preventing a viral infection or virus-related condition in an individual, comprising at least the steps of: a) determining the ability of a candidate compound to interact with CBP20 or CBP80 in a sample, and b) selecting the candidate compound that is determined to interact with CBP20 or CBP80 at step a).

24 Claims, 12 Drawing Sheets

Specification includes a Sequence Listing.

(58) Field of Classification Search
USPC .................................................. 435/7.1, 7.6
See application file for complete search history.

(56) References Cited

FOREIGN PATENT DOCUMENTS

| EP | 2465502 A1 | 6/2012 |
|---|---|---|
| EP | 2974729 A1 | 1/2016 |
| EP | 2975034 A1 | 1/2016 |
| EP | 3059236 A1 | 8/2016 |
| WO | 2004037976 A2 | 5/2004 |
| WO | 2010/143168 A2 | 12/2010 |
| WO | 2010/143169 A2 | 12/2010 |
| WO | 2012/080953 A1 | 6/2012 |
| WO | 2015/001518 A1 | 1/2015 |

OTHER PUBLICATIONS

English (machine) translation CN 1333270 (A), (Year: 2002).*
English (machine) translation CN 1333275 (A), (Year: 2002).*
International Search Report for PCT/EP2016/053533 dated Apr. 18, 2016 (6 pages).
Written Opinion for PCT/EP2016/053533 dated Apr. 18, 2016 (6 pages).
Bakkour et al., "Small-Molecule Inhibition of HIV pre-mRNA Splicing as a Novel Antiretroviral Therapy to Overcome Drug Resistance", PLoS Pathogens, Oct. 2007, vol. 3, No. 10, pp. 1530-1539.
Berges et al., "The utility of the new generation of humanized mice to study HIV-1 infection: transmission, prevention, pathogenesis, and treatment", Retrovirology, 2011, vol. 8, No. 65, pp. 1-19.
Denton el al., "Humanized Mouse Models of HIV Infection", AIDS Reviews., 2011, vol. 13, No. 3, pp. 135-148.
Hocine et al., "RNA Processing and Export", Cold Spring Harbor Perspectives in Biology, 2010, pp. 1-20.
Klinck et al., "Multiple Alternative Splicing Markers for Ovarian Cancer", Cancer Res., 2008, vol. 68, No. 3, pp. 657-663.
MacLean et al. "Effective of Collision Energy Optimizaton on the Measurement of Peptides by Selected Reaction Monitoring (SRM) Mass Spectrometry", Analytical Chemistry, 2010, vol. 82, No. 24, pp. 10116-10124.
Mazza et al., "Crystal Structure of the Human Nuclear Cap Binding Complex", Molecular Cell, Aug. 2001, vol. 8, No. 2, pp. 383-396.
Mazza et al., "Large-scale induced fit recognition of an m7GpppG cap analogue by the human nuclear cap-binding complex", The European Molecular Biology Organization Journal, 2002, vol. 21, No. 20, pp. 5548-5557.
McDougal et al., "Immunoassay for the Detection and Quantitation of Infectious Human Retrovirus, Lymphadenopathy-Associated Virus (LAV)", Journal of Immunological Methods, 1985, vol. 76, No. 1, pp. 171-183.
Nawroth et al., "Stable assembly of HIV-1 export complexes occurs cotranscriptionally", RNA, 2013, vol. 20, No. 1, pp. 1-8.
Nischang et al., "Humanized Mice Recapitulate Key Features of HIV-1 Infection: A Novel Concept Using Long-Acting Anti-Retroviral Drugs for Treating HIV-1", PLoS ONE, Jun. 2012, vol. 7, No. 6, pp. 1-12.
Olsen et el., "Parts per Million Mass Accuracy on an Orbitrap Mass Spectrometer via Lock Mass Injection into a C-trap*", Molecular & Cellular Proteomics, 2005, vol. 4, No. 12, pp. 2010-2021.
Schirle et al., "Mass Spectrometry-Based Proteomics in Preclinical Drug Discovery", Chemistry & Biology, Jan. 2012, vol. 19, No. 1, pp. 72-84.
Schoenberg et al., "Re-capping the message", Trends in Biochemical Sciences, Sep. 2009, vol. 34, No. 9, pp. 435-442.
Shevchenko et al., "Mass Spectrometric Sequencing of Proteins from Silver-Stained Polyacrylamide Gels", Analytical Chemistry, Mar. 1996, vol. 68. No. 5, pp. 850-858.
Taniguchi et al. "HIV-1 Rev protein specifies the viral RNA export pathway by suppressing TAP/NXF1 recruitment", Nucleic Acids Research, 2014, vol. 42, No. 10, pp. 6645-6658.
Tazi et al., "Alternative splicing: regulation of HIV-1 multiplication as a target for therapeutic action", The FEBS Journal, 2010, vol. 277, No. 4, pp. 867-876.
Venables et al., "Cancer-associated regulation of alternative splicing", Nature Structural & Molecular Biology, Jun. 2009, vol. 16, No. 6, pp. 670-881.
Worch et al., "Specificity of recognition of mRNA 5' cap by human nuclear cap-binding complex", RNA, 2005, vol. 11, No. 9, pp. 1355-1363.
Wu et al., "Fast and SNP-tolerant detection of complex variants and splicing in short reads", Bioinformatics, 2010, vol. 26, No. 7, pp. 873-881.

* cited by examiner

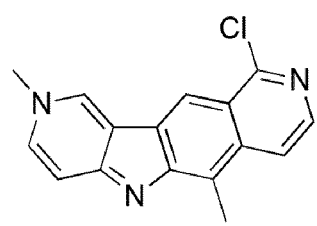 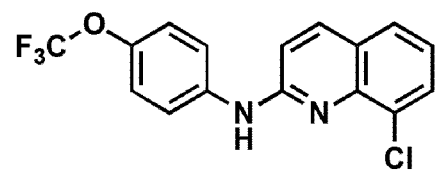
IDC16    Compound 1
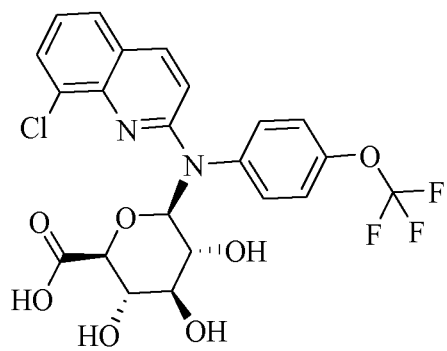
Compound 1-N glucuronide
Figure 1

A
Compound 1 efficacy on PBMCs
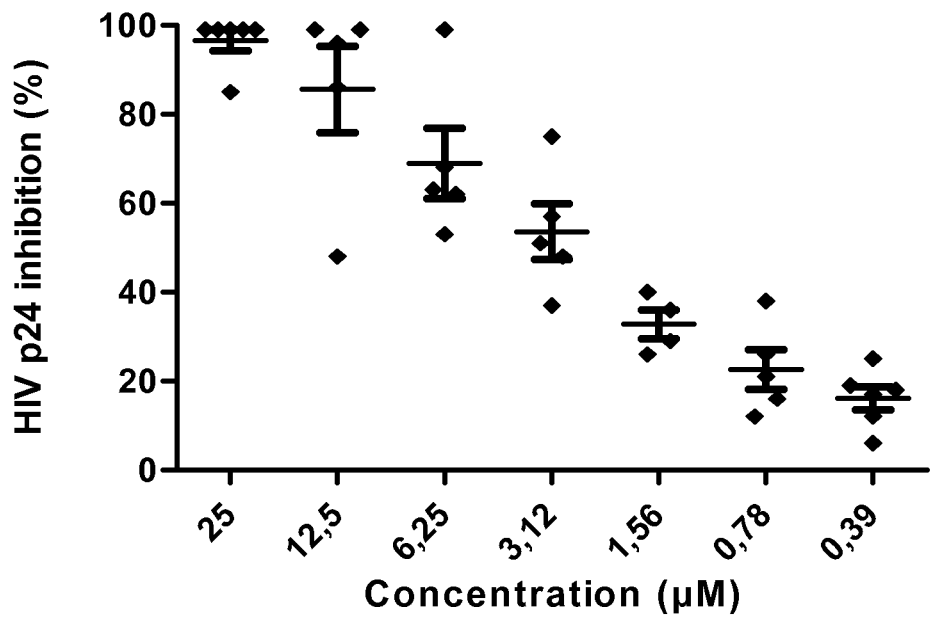
B
Compound 1 efficacy on macrophages
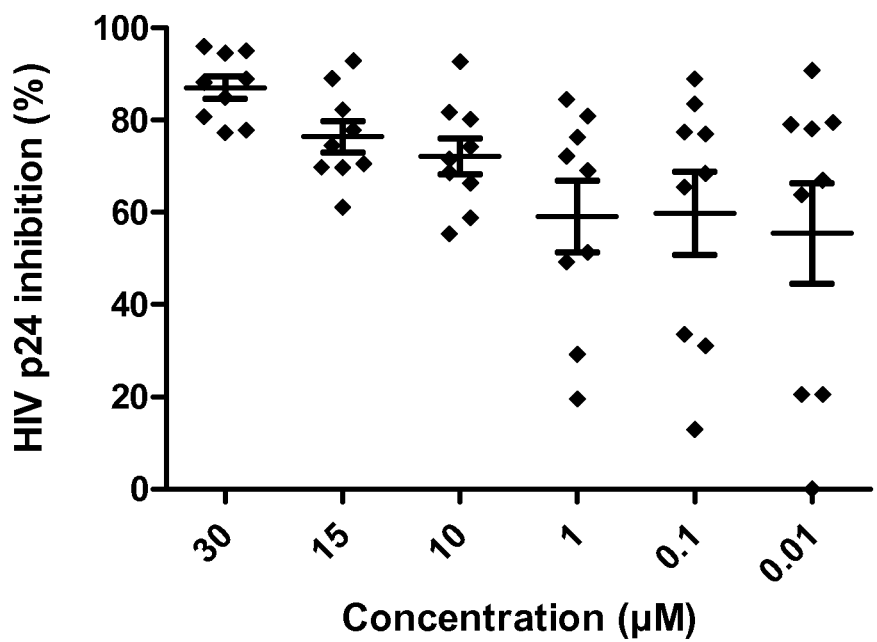
Figure 5

| HIV-1 strains | | % of inhibition with Compound 1 |
|---|---|---|
| HIV-1 B subtype | Ad8 | 71 ± 4 |
| | AdaM | 99 ± 1 |
| | Isolate B | 83 ± 8 |
| HIV-1 C subtype | Isolate C | 89 ± 1 |
| HIV-1 recombinants | CRF01 | 82 ± 11 |
| | CRF02 | 86 ± 3 |
| | CRF06 | 80 ± 5 |
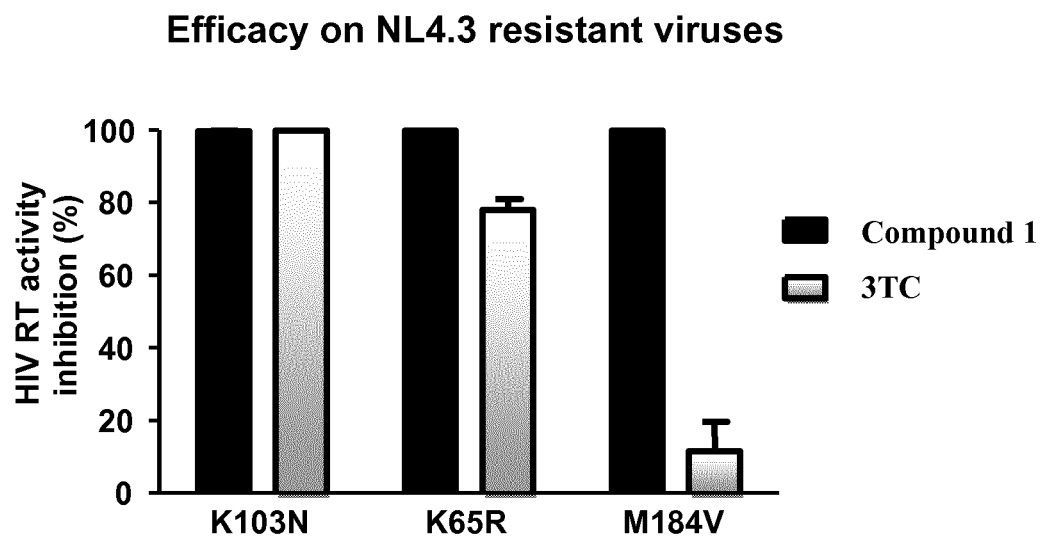
Figure 6A, B

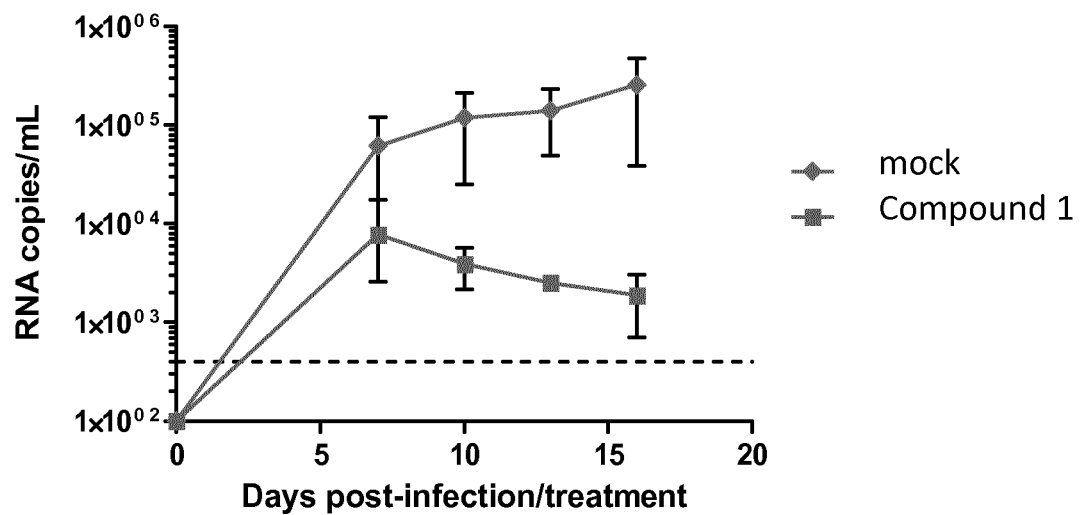
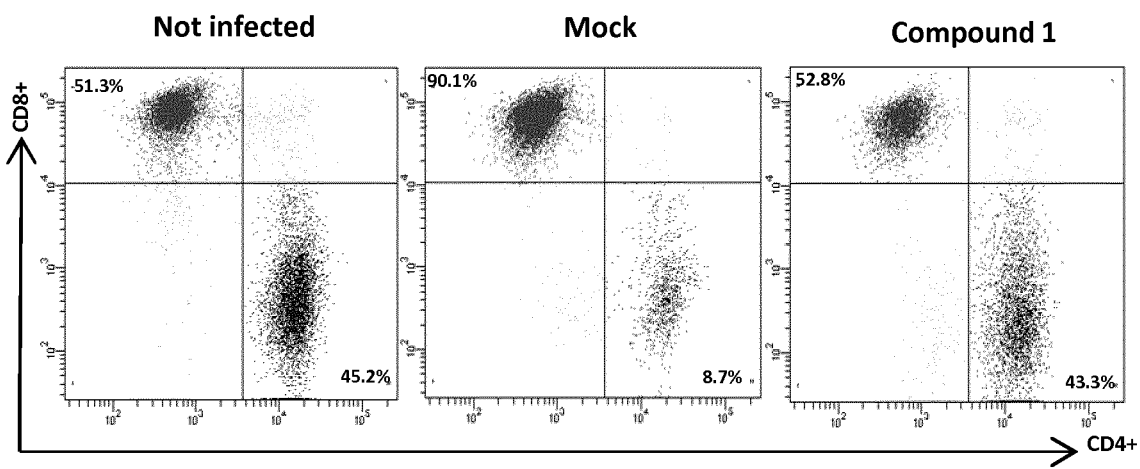
Figure 7A,B

METHODS FOR SCREENING COMPOUNDS FOR TREATING OR PREVENTING A VIRAL INFECTION OR A VIRUS-RELATED CONDITION

FIELD OF THE INVENTION

The invention relates to the field of methods for screening compounds which are useful for treating or preventing a viral infection or a virus-related condition. Compounds which have been selected with the aforementioned methods may provide durable control of viral rebound and/or a large spectrum of action with limited side effects.

BACKGROUND OF THE INVENTION

Viral replication relates to the formation of viruses during the infection process in the target host cells, which includes translation of viral RNAs by the endogenous machinery. In particular, many viral RNAs are translated and eventually processed through post-translational modifications before being exported outside of the nucleus.

The identification of compounds for treating or preventing a viral infection or a virus-related condition in an individual has led to the development of novel therapies.

Among virus-related conditions, AIDS has developed into a worldwide pandemic. Current therapies have succeeded in controlling the disease but long-term use of Anti-Retroviral Therapy (ART), which is a combination of 3TC, Raltegravir and tenofovir, is limited by issues of drug resistance and side effects.

What is more, those compounds do not necessarily inhibit the replication of viral strains harbouring mutations, which is prone to confer the development of resistant strains.

In particular, for HIV infections, the current ART drugs need to be taken for life and only attenuate the disease without curing it. One reason is that current Human Immunodeficiency Virus (HIV) therapies reduce viral load during treatment but titers rebound after treatment is discontinued, which is one of the consequences of virus latency.

Access to Highly Active Anti-Retroviral Therapy (HAART), based upon the combination of HIV protease and reverse transcriptase inhibitors, has dramatically changed the prognosis of HIV infection. As a result, HIV is considered as a chronic disease in developed countries. However, long-term use of HAART is limited by issues of drug resistance and side effects.

For example, resistance to new classes of anti-HIV/AIDS drugs such as Raltegravir® (integrase inhibitor) and Enfuvirtide® (entry inhibitor) has already been observed.

Alternatives to ART, for example including a combination 3TC-Tenofovir-Raltegravir and AZT (HAART), have thus been proposed.

One indole derivative (IDC16) was discovered to interfere with splicing enhancer activity of the SR protein splicing factor SRSF1 (see for reference Tazi et al. Alternative splicing: regulation of HIV-1 multiplication as a target for therapeutic action. *FEBS J*. 277, 867-876 (2010)). IDC16 is a planar fused tetracyclic indole compound. This compound suppresses the production of key viral proteins, thereby compromising subsequent synthesis of full-length HIV-1 pre-mRNA and assembly of infectious particles.

In order to minimize the risk that these indole derivatives intercalate between DNA bases, alternative compounds have been developed, that are particularly effective in treating diseases related to the splicing process, but which, in a surprising manner, have a cellular toxicity that is clearly less than the indole derivatives of the prior art.

WO2010/143169 reports compounds which have been found to be effective in treating AIDS and other diseases resulting from changes in splicing processes.

Such molecules, and in particular those in which the polyaromatic nucleus is further substituted by a positively charged (protonated aminoalkyl) side chain, have also been studied as potential anticancer agents (see also WO2010/143168). The guiding principle is that they intercalate DNA and exhibit cytotoxic effects by interfering with the function of DNA processing enzymes such as topoisomerase I and II. Unfortunately, this mechanism of action can still lead to adverse side effects.

Therefore, there is a continuing need for new compounds, in particular those acting through new and as yet unexplored mechanisms of action to treat or prevent viral infections, and more particularly to achieve HIV infection cure.

There also remains a need for compounds which deliver a long lasting reduction of the viral load after treatment termination, in particular for treating virus-infections which are associated with chronic treatment, and/or for targeting latent virus reservoirs.

There also remains a need for compounds with a large spectrum of action, but which are not prone to confer the development of resistant strains, and/or which do not lead to adverse effects.

There also remains a need for compounds which can be less frequently administered over a shorter period, or at longer intervals, than standard treatments; providing the potential to reduce healthcare costs and offer broader access to treatment.

Methods for screening compounds which are efficient for treating or preventing viral infections and virus-related conditions have been reported in the Art.

Recently, Taniguchi et al. (HIV-1 Rev protein specifies the viral RNA export pathway by suppressing TAP/NXF1 recruitment. Nucleic Acids Res. 42, 6645-6658 (2014)) has speculated that the remodeling activity of viral proteins Rev and Rex could be used as a target for anti-retroviral therapy, respectively for HIV and Human T-Lymphotropic Virus (HTLV). However, this document failed to identify compounds useful for therapy or prevention.

Thus, there remains a need for novel methods for screening compounds for treating or preventing a viral infection or a virus-related condition in an individual.

In particular, there remains a need for novel methods for eradicating a viral infection or a virus-related condition in an individual, including for eradicating HIV and/or as a cure for HIV.

SUMMARY OF THE INVENTION

The present invention relates to a method for screening a compound useful for treating or preventing a viral infection or virus-related condition in an individual, comprising at least the steps of:

a) determining the ability of a candidate compound to promote the interaction between CBP20 and CBP80 in a sample, and b) selecting the candidate compound that is determined at step a) to promote said interaction.

The present invention also relates to a method for screening a compound useful for treating or preventing a viral infection or virus-related condition in an individual, comprising at least the steps of:

a) determining the ability of a candidate compound to interact with CBP20 or CBP80 in a sample, and b) selecting the candidate compound that is determined at step a) to interact with CBP20 or CBP80.

BRIEF DESCRIPTION OF THE FIGURES

FIG. 1. Examples of quinoline derivative candidates for treating or preventing HIV-1 production in PBMC- and macrophages-infected cells. Drawing of 10-chloro-2,6-dimethyl-2H-pyrido[3',4':4,5]pyrrolo[2,3-g]isoquinoline (IDC 16), 8-chloro-N-(4-(trifluoromethoxy) phenyl)quinolin-2-amine (Compound 1) and 8-chloro-N-glucuronide-N-(4-(trifluoromethoxy)phenyl)quinolin-2-amine (Compound 1-N-glucuronide).

FIG. 5. Potency of indole derivatives to inhibit HIV-1 production in PBMC- and macrophages-infected cells. A) HIV-1 strain Ada-MR5 was used to infect triplicate of activated PBMCs from different donors (stimulated for two days with PHA and IL2) in the absence or presence of increasing concentrations of Compound 1. Supernatant was harvested 6 days post-infection (pi) and viral capsid protein p24 antigen was quantitated using standard ELISA protocol. Each point represents 6 donors. B) HIV-1 strain YU2 was used to infect triplicate of monocyte derived-macrophages from different donors in the absence or presence of increasing concentrations of Compound 1. Supernatant was harvested 8 days pi and viral capsid protein p24 antigen was quantitated using standard ELISA protocol. Each point represents 8 donors.

FIG. 6. HIV p24 inhibition of Compound 1 from different HIV-1 strains. A) Different HIV-1 strains (clade B, clade C and recombinants clades) were used to infect PBMCs from three different donors in the absence of presence of 5 µM of Compound 1. Supernatant was harvested 6 days pi and viral capsid protein p24 antigen was quantitated using standard ELISA protocol. B) RT activity (cpm) measured in human PBMCs infected with different resistant mutants of NL4.3 strain (K103N, K65R and M184V) and treated with Compound 1 or 3TC.

DETAILED DESCRIPTION OF THE INVENTION

Figure 2:
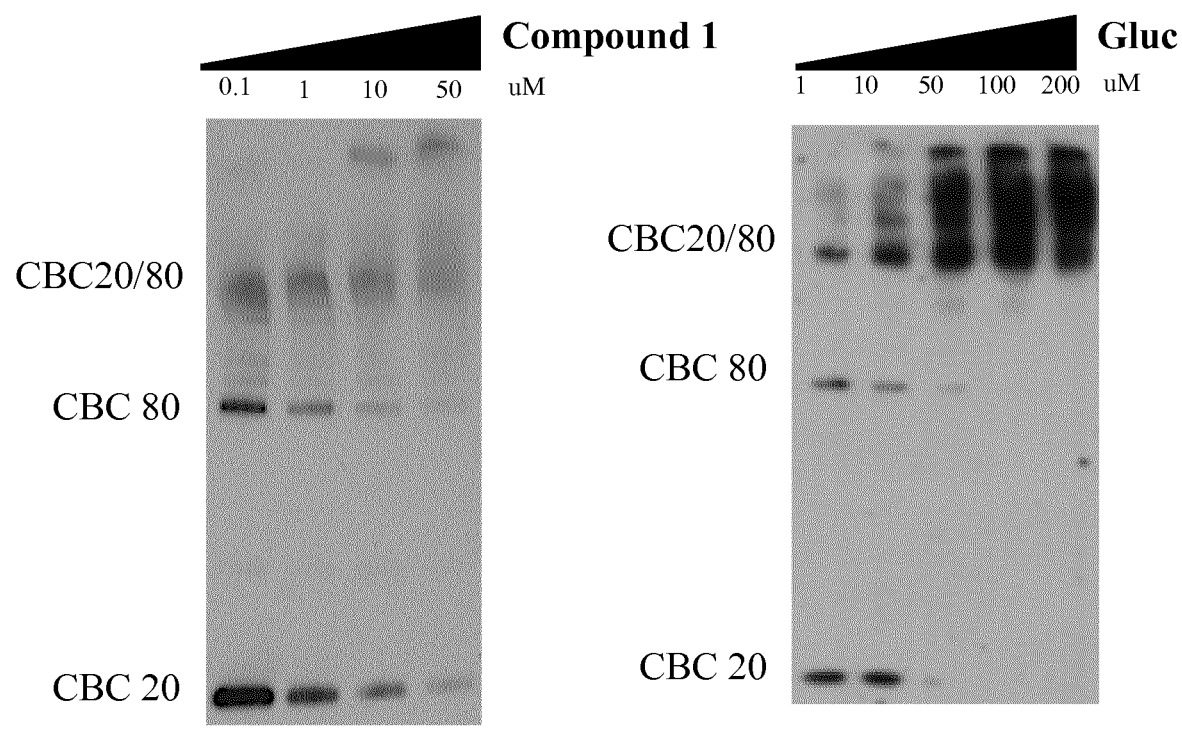
FIG. 2. Compound 1 interacts with the CBC complex. Purified recombinant CBP20 and CBP80 proteins were incubated with increasing concentrations of Compound 1 (left panel) or Compound 1-N-glucuronide (right panel, Gluc) and treated for 30 minutes with UV light. The proteins were revealed by Western Blotting using CBP20 and CBP80 antibodies. Left panel: from left to right, incubation with 0.1 (lane 1), 1 (lane 2), 10 (lane 3) and 50 µM (lane 4) of Compound 1. Right panel: from left to right, incubation with 1 (lane 1), 10 (lane 2), 50 (lane 3), 100 µM (lane 4) and 200 µM (lane 5) of Compound 1-N-glucuronide.

The present invention has for purpose to meet the aforementioned needs.

The Cap-Binding Complex (CBC) complex has a key role in several gene expression mechanisms, including transcription, splicing, transcript export and translation. It is mainly composed of the Cap-Binding Proteins CBP20 (CBC20) and CBP80 (CBC80) subunits. The CBC complex binds co-transcriptionally to the 5' cap of pre-mRNAs.

The 5' cap of endogenous pre-mature RNA transcripts is a post-translational modification that is essential for efficient gene expression, RNA stability and RNA export in eukaryotes (see Hocine et al.; "RNA Processing and Export"; Cold Spring Harb Perspect Biol.; 2010. See also Schoenberg et al.; "Re-capping the message"; Trends Biochem Sci.; 2009).

It has now been found that the Cap-Binding Complex (CBC) is a target for identifying compounds useful for treating or preventing a viral infection or a virus-related condition. In particular, it has now been found a link between (i) the ability of a compound to bind to the CBC complex, which includes CBP20 and CBP80 subunits and (ii) the ability of the said compound to treat or prevent a viral infection or a virus-related condition, in particular an HIV infection or AIDS, in an animal or in a human organism, as it will be further detailed in the present specification.

These surprising results have allowed the inventors to design methods for the screening of a candidate compound for its ability to treat or prevent a viral infection or a virus-related condition, which methods comprise (i) a step wherein the ability of the said candidate compound to interact with CBP20 or CBP80 subunits is determined or (ii) a step wherein the ability of the said candidate compound to promote the interaction between CBP20 and CBP80 is determined. Compounds that interact with CBP20 or CBP80 subunits as well as compounds that promote the interaction between CBP20 and CBP80 are shown herein as being active against the infection of an individual with a virus, which includes a retrovirus, and especially a HIV-1 virus.

As shown in the examples herein, a plurality of compounds that are able to modulate in vitro the interaction between recombinant CBP20 and CBP80 in the CBC complex have been selected. Using limited proteolysis, the inventors have shown that a small fragment of CBP20 starting from amino acid at position 37 to amino acid at position 66 may play an important role in the interaction of CBP20 with CBP80 within the CBC complex.

For reference, the amino acid sequence of human CBP20 is SEQ ID N° 1 (*Homo Sapiens* Nuclear cap-binding protein subunit 2).

The CBP20 fragment from position 37 to position 66 is the peptide of SEQ ID N° 2.

The amino acid sequence of CBP80 is disclosed as SEQ ID N° 3.

As it is shown in the examples herein, compounds that are determined to interact with CBP20 or CBP80, as well as compounds that are determined to promote the formation of the CBP20/CBP80 complex are useful for preventing or treating infections of an individual with a virus, which includes a retrovirus, and especially a HIV-1 virus.

As used herein, the term "individual" encompasses both human and animals.

Thus, the present invention relates to a method for screening a compound useful for treating or preventing a viral infection or virus-related condition in an individual, in particular an HIV infection or AIDS, comprising at least the steps of:

a) determining the ability of a candidate compound to promote the interaction between CBP20 and CBP80 in a sample, and b) selecting the candidate compound that is determined at step a) to promote said interaction.

The method described above may also be termed "first screening method" herein.

The present invention also pertains to a method for screening a compound useful for treating or preventing a viral infection or virus-related condition in an individual, in particular an HIV infection or AIDS, comprising at least the steps of:

a) determining the ability of a candidate compound to interact with CBP20 or CBP80 in a sample, and b) selecting the candidate compound that is determined at step a) to interact with CBP20 or CBP80.

The method described above may also be termed "second screening method" herein.

It is shown in the examples herein that a compound that is selected at step b) of either the first screening method or the second screening method described above (i) reduces intracellular virus replication, (ii) reduces virus replication in a virus-infected mammal.

More specifically, it is shown herein that a compound that is selected at step b) of either the first screening method or the second screening method described above (i) reduces HIV-1 replication in infected mammal cells, (ii) reduces HIV-1 viral load in HIV-1-infected mammals, and (iii) maintains or restores a high level of CD4+ cell count in HIV-1-infected mammals.

As used herein, the terms «interaction» or «interacting«, as applied to protein or peptide interaction, encompass both direct and indirect interaction of one protein or peptide with another protein or peptide; however, these terms preferably relate to a direct interaction of one protein or peptide with another protein or peptide. Protein-Protein interactions may encompass stable, strong, transient or weak interactions.

As used herein, a «direct interaction» has the same meaning as «binding«, and encompasses in particular the binding of one protein or peptide with another protein or peptide through salt bridges, hydrogen bonding, electrostatic interaction, hydrophobic interaction, Van der Waals interaction and covalent coupling.

As used herein, «promoting an interaction» encompasses increasing the likelihood of an interaction to occur, and/or stabilizing an existing interaction, either directly or indirectly. In particular, and based on the examples, the expression «promoting an interaction» encompasses increasing the amount of a protein complex comprising CBP20 and CBP80, starting from a pre-determined amount of monomeric CBP20 and CBP80.

The inventors also provide evidence that, by modulating the formation of the CBC complex, and more particularly by promoting the interaction of CBP20 and CBP80, it is possible to alter specifically the splicing and the export of viral mRNAs, but not of other non-viral mRNAs, or at least to a lesser extent. Thus, the CBC complex is a particularly promising target to identify novel compounds having reduced cytotoxicity, long-term efficiency, large spectrum of action and which do not select mutant virus strains.

It has further been shown that compounds that are selected at step b) of the first screening method or the second screening method described herein, are efficient in inhibiting viral replication by modulating the splicing machinery, and/or by preventing export of unspliced viral transcripts. Retained viral RNA is massively spliced but importantly, normal cellular splicing is unaffected by the screened compounds, including Compound 1 and its glucuronidated derivative, the Compound 1-N-glucuronide.

Without wishing to be bound by any particular theory, it is believed that the fragment of CBP20 from position 37 to 66 encompasses a site that is critical for the activity of the CBC complex, including the interaction of CBP20 with CBP80.

As used herein, «determining» also encompasses "measuring".

As used herein, «screening» also encompasses "evaluating".

As used herein, «preventing» also encompasses «reducing the likelihood of occurrence» or «reducing the likelihood of reoccurrence«.

As used herein, «sample» encompasses any biological or non-biological sample, including any biopsy sample, blood-derived or urine sample, saliva, spinal fluid, pulmonary, nasal, vaginal, ocular, peritoneal, throat, urethral, cell or tissue sample, cell culture and/or fraction thereof. The sample may be previously collected from the individual for whom the efficiency of the candidate compound must be determined, or from another individual, and/or a group of individuals.

As used herein, a "non-biological sample" encompasses a sample which contains CBP20 or CBP80 or both CBP20 and CBP80, depending of the invention's screening method that is being performed, which sample has not been previously collected from an individual. Illustratively, a non-biological sample encompasses samples comprising recombinant or synthetic CBP20, CBP20 native or modified fragment, recombinant or synthetic CBP80, CBP80 native or modified fragment, or a combination of recombinant or synthetic CBP20 and recombinant or synthetic CBP80.

As used herein, a "biological sample" consists of, or derives from, a sample that has been previously collected from an individual. A biological sample derives from a sample that has been previously collected from an individual when the said previously collected samples has been subjected to one or more pre-treatment steps (e.g. concentration, extraction, stabilization, etc.) in order to obtain the biological sample that is used in as screening method described herein.

A biological sample previously collected from an individual is preferably used for the purpose of selecting relevant compounds that are preventively or therapeutically active in the said individual.

As used herein, a biological sample consists of, or derives from, a sample collected in an individual, namely a mammal, which encompasses a human mammal and a non-human mammal.

As used herein, "selecting the candidate compound" encompasses determining that the candidate compound is a compound useful for treating or preventing a viral infection or virus-related condition.

Noticeably, a plurality of compounds is described herein (i) that interact with CBP20, (ii) that interact with CBP80 and (iii) that promote the interaction between CBP20 and CBP80.

As a consequence the said illustrative compounds (i) may be selected according to the first screening method described herein, (ii) may also be selected according to the second screening method described herein, wherein the ability of the said compounds to interact with CBP20 is determined at step a) and (iii) may equally be selected according to the second screening method described herein, wherein the ability of the said compounds to interact with CBP80 is determined at step a).

Thus, according to another aspect, the present invention also concerns a method for screening a compound useful for treating or preventing a viral infection or virus-related condition in an individual, in particular an HIV infection or AIDS, comprising at least the steps of:

a1) determining the ability of a candidate compound to promote the interaction between CBP20 and CBP80 in a first sample, a2) determining the ability of the candidate compound to interact with CBP20 or CBP80 in a second sample, and b) selecting the candidate compound that is determined to promote said interaction between CBP20 and CBP80, or alternatively that is determined to interact with CBP20 or CBP80; wherein step a1) and step a2) occur in that order or in the inverse order, with the first and second sample being the same sample or distinct samples.

According to some embodiments, the candidate compound is selected when it is determined to both (i) promote the interaction between CBP20 and CBP80 at step a1), and (ii) interact with CBP20 or CB80.

As used herein, a compound that interacts with CBP20 or CBP80 encompasses a compound that both (i) interacts with CBP20 and (ii) interacts with CBP80.

As used herein, "determining the ability of a candidate compound" encompasses (i) determining the ability of the candidate compound from previously measured interaction data; and (ii) measuring the ability of the candidate compound.

The above mentioned methods may all comprise at least one step of measuring the ability of a candidate compound to promote the interaction between CBP20 and CBP80 in said sample of interest.

Thus, according to said first aspect, the invention relates to a method for screening a compound useful for treating or preventing a viral infection or virus-related condition in an individual, in particular an HIV infection or AIDS, comprising at least the steps of:

a) measuring the ability of a candidate compound to promote the interaction between CBP20 and CBP80 in a sample, and b) selecting the candidate compound that promotes said interaction.

Also, the above mentioned methods may all comprise at least one step of measuring the ability of a candidate compound to interact with CBP20 or CBP80 in said sample.

Thus, according to said second aspect, the invention relates to a method for screening a compound useful for treating or preventing a viral infection or virus-related condition in an individual, in particular an HIV infection or AIDS, comprising at least the steps of:

a) measuring the ability of a candidate compound to interact with CBP20 or CBP80 in a sample, and b) selecting the candidate compound that interacts with CBP20 or CBP80.

In particular, the above-mentioned methods may all comprise a step of determining the ability of the compound to interact with CBP20 in a sample.

Thus, the invention also relates to a method for screening a compound useful for treating or preventing a viral infection or virus-related condition in an individual, in particular an HIV infection or AIDS, comprising at least the steps of:

a) measuring the ability of a candidate compound to interact with CBP20 in a sample, and b) selecting the candidate compound that interacts with CBP20.

According to some embodiments, the above-mentioned methods may all comprise a step a0) of providing a sample.

Thus, the invention also relates to a method for screening a compound useful for treating or preventing a viral infection or virus-related condition in an individual, in particular an HIV infection or AIDS, comprising at least the steps of:

a0) providing a sample, a1) measuring the ability of a candidate compound to promote the interaction between CBP20 and CBP80 in said sample, and b) selecting the candidate compound that promotes said interaction.

Thus, the invention also relates to a method for screening a compound useful for treating or preventing a viral infection or virus-related condition in an individual, in particular an HIV infection or AIDS, comprising at least the steps of:

a0) providing a sample, a1) measuring the ability of a candidate compound to interact with CBP20 or CBP80 in said sample, and b) selecting the candidate compound that interacts with CBP20 or CBP80.

More particularly, the above-mentioned methods may all comprise a step of determining or measuring the ability of the candidate compound to interact with a fragment of CBP20 which binds to CBP80.

Alternatively, the above-mentioned methods may all comprise a step of determining or measuring the ability of the candidate compound to interact with a fragment of CBP80 which binds to CBP20.

Critical residues of CBP20 which have been found to be involved in the interaction with CBP80 are known in the Art. For reference, Mazza et al. (Crystal structure of the human nuclear cap binding complex. Mol. Cell 8, 383-396 (2001) reports the crystal structure (PDB: 1H6K) of the mildly trypsinized CBP20/CBP80 complex and identifies critical residues which are involved in the interaction between CBP80 and CBP20, either through salt bridges or through hydrogen bonds.

Preferably, the fragment of CBP20 which binds to CBP80 includes amino acid position 20 to amino acid position 110 of CBP20, wherein CBP is established for reference as SEQ ID N° 1; and even more preferably amino acid position 38 to amino acid position 119 of SEQ ID N° 4, which includes amino acid position 38 to amino acid position 67 of SEQ ID N° 2.

The above-mentioned methods may further comprise a step of determining or measuring the ability of the candidate compound to not interact with the cap binding site of CBP20, and selecting the candidate compound that does not interact with said cap binding site of CBP20.

Indeed, the experimental evidence (see example 1) shows that the screened compound 1 does not interact with the cap binding site of CBP20, and does not inhibit the binding of capped RNA to CBP20. Without wishing to be bound by any particular theory, it is believed that this property further favors a selection of compounds having better specificity for preventing viral RNA export, over non-viral RNA export.

Methods for determining or measuring the ability of the candidate compound to not inhibit the binding of capped RNA to the CBC complex, including CBP20, or even to not interact with the cap binding site of CBP20, are disclosed in the examples, and in Mazza et al. (Crystal structure of the human nuclear cap binding complex. Mol. Cell 8, 383-396 (2001)) and in Mazza (2) et al. (Large-scale induced fit recognition of an m(7)GpppG cap analogue by the human nuclear cap-binding complex. EMBO J. 21, 5548-5557 (2002)).

For reference, a fragment of CBP20 encompassing the Cap-binding site is of sequence SEQ ID N° 4, which includes amino acid position 38 to amino acid position 119.

According to one exemplary embodiment, the ability of the candidate compound to not inhibit the binding of capped RNA to the CBC complex can be determined by a competition assay, which may comprise a step of competing the complex formed between CBC and capped RNA with a cap analog such as $m^7GpppG$ and comparing it to a reference value.

The methods of the invention are particularly amenable for high-throughput studies, including in vitro high-throughput studies.

According to one embodiment, CBP20 and/or CBP80 are synthetic and/or recombinant polypeptides; or fragments thereof.

In the sense of the invention, "recombinant polypeptides" encompass polypeptides that were produced from an organism that does not naturally produce said polypeptides.

According to one embodiment, CBP20 and/or CBP80 are purified polypeptides; or fragments thereof.

In the sense of the invention, "purified polypeptides" encompass polypeptides that are present in a sample in an isolated form.

According to one embodiment, the sample comprises purified recombinant CBP20 and/or purified recombinant CBP80.

Rev-Mediated Export of Viral RNAs.

Rev (also called p19) is a HIV protein that plays a key role in virus replication, in particular by promoting the export to the cytoplasm of unspliced or singly-spiced RNAs. As a consequence, Rev also promotes the expression of HIV proteins.

Without wishing to be bound by any particular theory, the inventors believe that compounds that are selected at step b) of the first screening method or the second screening method described herein, are also particularly useful for modulating the activity of Rev, in particular for decreasing the activity of Rev including Rev-mediated export of viral RNAs.

Without wishing to be bound by any particular theory, the inventors also believe that at least some of the compounds that are selected at step b) of the first screening method or the second screening method described herein, may also interact directly or indirectly with Rev, due to the ability of the screened Compound 1 to 1) prevent Rev-mediated export of viral RNAs and 2) prevent RNA splicing in vivo; and also because Rev interacts with the CBC complex.

Rev-mediated export of viral RNAs refers to the export to the cytoplasm of unspliced or singly-spiced RNAs that is associated with the presence and/or the expression of Rev in said sample.

According to some embodiments, the in vivo, in vitro or in silico methods of the invention may thus comprise the steps of:

(i) determining the ability of a candidate compound to interact with Rev; and (ii) selecting the candidate compound that is determined at step (i) to interact with Rev.

According to some embodiments, the in vivo, in vitro or in silico methods of the invention may also comprise the steps of:

(i) determining the ability of a candidate compound to modulate, and preferably decrease, the activity of Rev in a sample; and (ii) selecting the candidate compound that is determined at step (i) to modulate, preferably decrease, said activity.

According to some embodiments, the in vivo, in vitro or in silico methods of the invention may thus comprise the steps of:

(i) determining the ability of the candidate compound to interact with Rev; and/or to decrease the activity of Rev;

(ii) selecting the candidate compound that is determined to interact with Rev and/or to decrease the activity of Rev at step (i).

In the sense of the invention, the "activity of Rev" encompasses (i) promoting the export of viral RNAs; and (ii) preventing RNA splicing.

Determining the activity of Rev in a sample may thus encompass:

(1) determining the concentration of Rev;
(2) determining the expression of Rev;
(3) determining the interaction of Rev with CBC, including the interaction of Rev with CBP20 or CBP80;
(4) determining the interaction of Rev with splicing factors, including ASF1/SF2 (Serine/Arginine-rich splicing factor 1 or SFRS1);
(5) determining the interaction of Rev with a Rev Response Element (RRE) sequence;
(6) determining the Rev-mediated export of viral RNAs;
(7) determining the Rev-mediated inhibition of RNA splicing;
(8) determining the localization of Rev; and/or
(9) determining the interaction of Rev with the NES receptor CRM1.

Other examples of splicing factors which are known to interact with Rev include: hnRNP A1 and splicing factor p32.

In the sense of the invention, "determining the expression of Rev", encompasses determining the concentration of a nucleic acid encoding Rev.

In the sense of the invention, "Rev-mediated", such as in "Rev-mediated export" or "Rev-mediated inhibition" means that it is associated with the presence of Rev. Accordingly, establishing whether Rev is associated with export of viral RNAs and/or inhibition of RNA splicing is known in the Art, and may for instance rely on a step of comparing the activity of the candidate compound to a reference value that is determined on a sample which does not comprise and/or express Rev.

Accordingly, determining the ability of a candidate compound to decrease the activity of Rev in a sample encompasses determining the ability of said candidate compound to:

(1) decrease the concentration of Rev in said sample;
(2) decrease the expression of Rev in said sample;
(3) promote the interaction of Rev with CBC, including the interaction of Rev with CBP20 or CBP80, in said sample;
(4) promote the interaction of Rev with splicing factors, including ASF1/SF2 (Serine/arginine-rich splicing factor 1 or SFRS1) in said sample;
(5) decrease the interaction of Rev with a RRE sequence in said sample;
(6) decrease the Rev-mediated export of viral RNAs in said sample;
(7) decrease the Rev-mediated inhibition of RNA splicing in said sample;
(8) decrease the interaction of Rev with the NES receptor CRM1; and/or
(9) modulate the localization of Rev.

For reference, a DNA nucleic acid sequence corresponding to a Rev Response Element (RRE) is a nucleic acid of sequence SEQ ID N° 5.

For reference, the sequence of a nucleic acid coding for Rev is SEQ ID N° 6.

Methods for determining a concentration or an expression of a protein in a sample are known in the Art. Methods for determining protein-protein interactions or protein-nucleic acid interactions are also known in the Art, as detailed hereafter and in the examples.

According to one exemplary embodiment, the Rev-mediated export of viral RNAs, is assessed using a HIV reporter system, comprising:

5' and 3' HIV Long Terminal Repeats (LTRs);
one or more RRE elements
one or more MS2 binding sites.

Figure 8A:
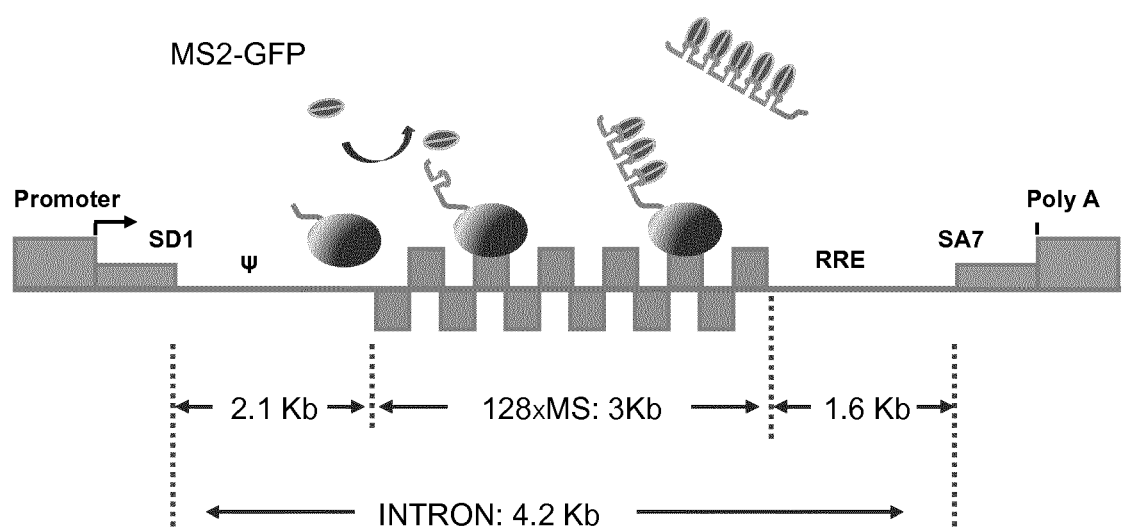
FIG. 8. Compound 1 influences Rev-mediated HIV RNA biogenesis and export. A) Schematic representation of the HIV-1 reporter gene B) Visualization of GFP-MS2-Bound RNA in HeLa cells expressing tat, MS2-GFP and HIV-reporter transcripts in non transfected or transfected cells with Rev. Rev-transfected cells were untreated (DMSO) or treated with Compound 1. Arrow indicates transcription site. C) Quantitation of images corresponding to untreated (DMSO) or treated (Compound 1) in (B), in terms of: total GFP (upper panel) expressed in RFU or Relative Fluorescence Units; in the nucleoplasm (middle panel) expressed in Number of Foci in Rev-transfected cells; or at the start site (lower panel) expressed as a percentage of nuclei with a starting transcription point. Box-plots show the average GFP intensity (foci numbers or starting transcription point numbers) of Rev-transfected HeLa cells for each condition. Whiskers correspond to the minimum and maximum, boxes, to the 25-75 percentiles and the band inside the box, to the median. Statistical analysis was performed on at least 15 nuclei of Rev positive cells using an unpaired/t/-test.

Examples of such HIV reporter systems are disclosed in FIG. 8A, in Example 4 and in Nawroth et al. (Stable assembly of HIV-1 export complexes occurs cotranscriptionally, RNA, 20, 1-8 (2014). According to said exemplary embodiment, the HIV reporter system is then transfected into a cell expressing the HIV protein Tat and MS2, either in native or in a recombinant form that is suitable for visualization (i.e. MS2 coupled with a fluorescent protein such as GFP).

According to another exemplary embodiment, the Rev-mediated inhibition of RNA splicing is assessed by RT-PCR, and/or deep sequencing as shown in Example 5.

The above-mentioned methods, which include a step of determining the ability of a compound to modulate the activity of Rev may also be used as independent methods for screening a compound useful for treating or preventing a viral infection or a virus-related condition in an individual.

Viruses

The methods of the invention are suitable for screening compounds useful for treating or preventing a viral infection or a virus-related condition.

In a non-limitative manner, examples of viruses which are considered by the invention include enveloped and naked viruses, which includes DNA viruses, RNA viruses and retroviruses, which includes dsDNA viruses, ssDNA viruses, dsRNA viruses, (+)ssRNA viruses, (−)ssRNA viruses, ssRNA-RT viruses and dsDNA-RT viruses, which includes oncoviruses, lentiviruses and spumaviruses.

Examples of viruses include latent viruses and/or viruses associated with chronic infection and/or retroviruses.

The oncoviruses are thus termed because they can be associated with cancers and malignant infections. There may be mentioned, for example, leukemogenic viruses (such as the avian leukemia virus (ALV), the murine leukemia virus (MULV), also called Moloney virus, the feline leukemia virus (FELV), human leukemia viruses (HTLV) such as HTLV1 and HTLV2, the simian leukemia virus or STLV, the bovine leukemia virus or BLV, the primate type D oncoviruses, the type B oncoviruses which are inducers of mammary tumors, or oncoviruses which cause a rapid cancer (such as the Rous sarcoma virus or RSV).

The spumaviruses manifest fairly low specificity for a given cell type or a given species, and they are sometimes associated with immunosuppressive phenomena; that is the case, for example, for the simian foamy virus (or SFV).

The lentiviruses, such as HIV, are thus named because they are responsible for slow-progressing pathological conditions which very frequently involve immunosuppressive phenomena, including AIDS.

Viruses, and in particular retroviruses such as HIV, HTLV-I and HTLV-II, are known to rely upon RNA splicing and splicing regulation in order to spread and disseminate within cells and tissues of an infected individual. Other viruses of interest are viruses pathogenic for human, including but not limited to HSV family viruses (including 1, 2, 6), CMV, VZV, HBV, HCV, Hepatitis E virus, Papilloma viruses, RSV, Rhino viruses, influenza viruses, adenoviruses, EBV, Ebola, Nipah viruses, and other arboviruses, Dengue, Chikungunya, West Nile viruses, Rift valley virus, Japanese encephalitis virus, SRAS other coronaviruses, parvovirus, enteroviruses.

Other viruses of interest are viruses pathogenic for animals, including, but not limited to, influenza, FLV, pestivirus, Hantavirus, and lyssavirus.

In particular, viruses and virus-related conditions which are considered include viruses of which viral replication requires RNA splicing, and/or viral RNA export from the nucleus to the cytoplasm.

Viruses which are more particularly considered are RNA viruses and retroviruses, including lentiviruses, and preferably HIV. Accordingly, virus-related conditions which are more particularly considered are associated with a RNA virus or a retrovirus, and preferably HIV.

HIV may include HIV-I, HIV-2 and all subtypes thereof, which includes HIV-I strains belonging to the HIV-I B subtype, HIV-I C subtype, and HIV-I recombinants. Examples include HIV-I strains selected from Ad8, AdaM, Isolate B, Isolate C, CRF01, CRF02 and CRF06.

Advantageously, viruses may include HIV-strains which have developed resistances for current treatments.

According to a preferred embodiment, the virus-related condition is AIDS.

Methods for Determining Protein-Protein Interactions

The above-mentioned methods include a step of:

(i) determining or measuring the ability of a candidate compound to promote the interaction between CBP20 and CBP80 in a sample; and/or (ii) determining or measuring the ability of a candidate compound to interact with CBP20 or CBP80 in a sample.

According to some embodiments, the methods include a step of determining or measuring a variation of the interaction between CBP20 and CBP80, either in the presence or in the absence of the candidate compound.

According to some embodiments, the methods include a step of determining or measuring a variation of the interaction between CBP20 and the candidate compound.

According to some embodiments, the methods include a step of determining or measuring the interaction between CBP80 and the candidate compound.

The above-mentioned embodiments may be further combined in a single method.

Protein-protein interactions may be determined and/or measured either qualitatively, or quantitatively.

Qualitative determination or measurement of protein-protein interactions may thus comprise or consist of detecting the occurrence of an interaction.

In a non-limitative manner, quantitative determination or measurement of protein-protein interactions may thus comprise or consist of determining or measuring a dissociation constant ($K_d$), an association constant ($K_a$), an on-rate constant ($k_{on}$) and/or an off-rate constant ($k_{off}$), either in the presence or in the absence of the candidate compound.

Alternatively, determining or measuring a protein-protein interaction may include a step of determining or measuring the concentration of a complex formed by the said proteins, either in the presence or in the absence of the candidate compound.

Thus, the screening methods may rely on methods for determining protein-protein interactions, such as in vivo or in vitro or in silico methods; which includes methods wherein the interaction is determined by at least one technique selected from: limited proteolysis, co-immunoprecipitation, Bimolecular Fluorescence Complementation (BiFC), Fluorescence Resonance Energy Transfer (FRET), Radioimmunoassay, ELISA, Yeast two-Hybrid (Y2H) and Protein-fragment Complementation Assay (PCA), Affinity Electrophoresis or Gel-mobility shift assay, affinity chromatography, pull-down assay, co-immunoprecipitation, phage display, chemical crosslinking, tandem affinity purification (TAP), Microscale Thermophoresis (MST), Surface Plasmon Resonance (SPR), Fluorescence Anisotropy, Isothermal Titration calorimetry (ITC), Mass Spectrometry, X-ray crystallography, Nuclear Magnetic Resonance (NMR), Electron Microscopy and Protein Docking.

In the sense of the invention, "protein docking", encompasses computer-assisted prediction of drug or compound to protein, and protein-protein interactions.

All those methods are known in the Art, and may be used either for determining the presence or the absence of an interaction between one or more proteins, peptides, or fragments thereof.

According to preferred embodiments, the interaction is determined or measured by at least one technique selected from: limited proteolysis, co-immunoprecipitation, pull-down assay, chemical crosslinking, Surface Plasmon Resonance (SPR), Fluorescence Anisotropy, Isothermal Titration calorimetry (ITC), and Protein Docking.

According to exemplary embodiments, the interaction is determined or measured by at least one technique selected from: limited proteolysis, Affinity Electrophoresis or Gel-mobility shift assay, chemical crosslinking and Mass Spectrometry.

According to some embodiments, Affinity Electrophoresis and Gel-mobility shift assays may be achieved in native or denaturing conditions, including PAGE and SDS-PAGE electrophoresis.

Examples of suitable protocols for Limited proteolysis and Gel-mobility shift assays are described in the examples, and in Mazza et al. (Large-scale induced fit recognition of an m(7)GpppG cap analogue by the human nuclear cap-binding complex. EMBO J. 21, 5548-5557 (2002)).

Candidate Compounds

The above-mentioned methods are particularly suitable for selecting candidate compounds for treating or preventing a viral infection or a virus-related condition.

Also, the above-mentioned methods are particularly suitable for selecting candidate compounds having a large spectrum of action, but which are not prone to confer the development of resistant strains, and/or which do not lead to adverse effects.

Also, the above-mentioned methods are particularly suitable for selecting candidate compounds which can be less frequently administered and/or over a shorter period than standard treatments.

Also, the above-mentioned methods are particularly suitable for selecting candidate compounds for increasing the CD4+ cell count and/or decreasing the viral load in an HIV/AIDS infected individual, and/or for decreasing or even suppressing HIV replication in an HIV/AIDS infected individual.

Also, the above-mentioned methods are particularly suitable for selecting candidate compounds for treating a latent virus infection in an individual, in particular for treating a latent HIV infection.

Also, the above-mentioned methods are particularly suitable for selecting candidate compounds for eradicating a viral infection or a virus-related condition in an individual, including for eradicating HIV and/or as a cure for HIV.

Also, the above-mentioned methods are particularly suitable for selecting candidate compounds for treating or preventing a viral infection or a virus-related condition in treatment-resistant individuals, especially individuals infected with a resistant HIV-strain, including HAART-resistant and ART-resistant individuals.

Thus, the above-mentioned methods are particularly suitable for selecting candidate compounds for treating or preventing a viral infection or a virus-related condition in treatment-resistant individuals, in particular selected from: Lamivudin (3TC)-resistant, Tenofovir-resistant, Raltegravir-resistant and Azidothymidine (AZT)-resistant individuals.

The candidate compounds may be either artificial (i.e. non-naturally occurring) or natural compounds.

By targeting specifically a finite library of candidate compounds, it is thus possible to improve the scalability of the screening methods, notably in the context of high-throughput screening procedures.

Libraries of candidate compounds which are disclosed hereafter are also particularly useful for methods which include a step of determining the ability of a candidate compound to modulate the activity of Rev.

Candidate compounds, and their pharmaceutically acceptable salts, which are particularly useful in the screening methods of the invention are thus disclosed hereafter.

The candidate compounds are preferably quinoline derivatives selected from compounds disclosed in the following applications: WO2010/143169, WO2012080953, EP14306164, and EP14306166.

According to one general embodiment, the candidate compounds to be screened are quinoline derivatives selected from any one of the compounds of formula:

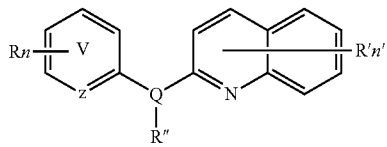

wherein:

z represents N or C,

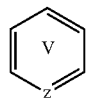

means an aromatic ring wherein V is C or N and when V is N, V is in ortho, meta or para of z, i.e. forms respectively a pyridazine, a pyrimidine or a pyrazine group, R independently represent a hydrogen atom, a halogen atom or a group chosen among a —CN group, a hydroxyl group, a —COOR$_1$ group, a (C$_1$ C$_3$)fluoroalkyl group, a (C$_1$ C$_3$)fluoroalkoxy group, a (C$_3$-C$_6$)cycloalkyl group, a —NO$_2$ group, a —NR$_1$R$_2$ group, a (C$_1$ C$_4$)alkoxy group, a phenoxy group, a NR$_1$SO$_2$NR$_1$R$_2$ group, a —NR$_1$SO$_2$R$_1$ group, a NR$_1$C(=O) R$_1$ group, a NR$_1$C(=O)—NR$_1$R$_2$ group, a SO$_2$NR$_1$R$_2$ group, a SO$_3$H group, a O—SO$_2$—OR$_3$ group, a OP(=O) (OR$_3$)(OR$_4$) group, a —O—CH$_2$—COORS group and a (C$_1$ C$_3$)alkyl group, said alkyl being optionally mono-substituted by a hydroxyl group, Q is N or O, provided that R" does not exist when Q is O, R$_1$ and R$_2$ are independently a hydrogen atom or a (C$_1$-C$_3$)alkyl group, R$_3$ and R$_4$ independently represent a hydrogen atom, Li+, Na+, K+, N+(Ra)$_4$ or a benzyl group, n is 1, 2 or 3, n' is 1, 2 or 3, R' independently represent a hydrogen atom or a group chosen among a (C$_1$ C$_3$)alkyl group, a halogen atom, a hydroxyl group, a —COOR$_1$ group, a —NO$_2$ group, a NR$_1$R$_2$ group, a morpholinyl or a morpholino group, a N-methylpiperazinyl group, a (C$_1$ C$_3$)fluoroalkyl group, a (C$_1$ C$_4$)alkoxy group and a —CN group, and can further be a group chosen among:

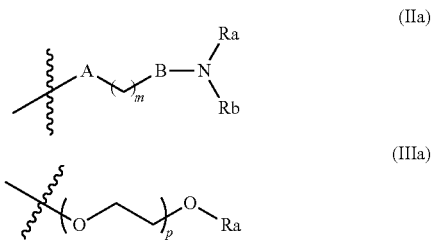

A is a covalent bond, an oxygen atom or NH,

B is a covalent bond or NH, m is 1, 2, 3, 4 or 5, p is 1, 2 or 3,

Ra and Rb independently represent a hydrogen atom, a (C$_1$ C$_5$)alkyl group or a (C$_3$C$_6$)cycloalkyl group, Ra and Rb can further form together with the nitrogen atom to which they are attached a saturated 5- or 6-membered heterocycle optionally containing a further heteroatom chosen among N, O and S, said heterocycle being optionally substituted by one or more Ra, provided that when R' is a group (IIa) or (IIIa), n' may be 2 or 3 only if other R' groups are different from said group (IIa) or (IIIa), R" is a hydrogen atom, a (C$_1$-C$_4$)alkyl group or is a group (IIa) as defined above, or anyone of its pharmaceutically acceptable salt;

or alternatively wherein the candidate compound is of formula:

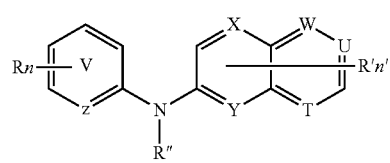

wherein:

means an aromatic ring wherein V is C or N and when V is N, V is in ortho, meta or para of Z, i.e. forms respectively a pyridazine, a pyrimidine or a pyrazine group, R independently represent a hydrogen atom, a halogen atom or a group chosen among a —CN group, a hydroxyl group, a —COOR$_1$ group, a (C$_1$-C$_3$)fluoroalkyl group, a (C$_1$-C$_3$)fluoroalkoxy group, a —NO$_2$ group, a —NR$_1$R$_2$ group, a (C₁-C₄)alkoxy group, a phenoxy group and a (C₁-C₃)alkyl group, said alkyl being optionally mono-substituted by a hydroxyl group, R₁ and R₂ are independently a hydrogen atom or a (C₁-C₃)alkyl group, n is 1, 2 or 3, n' is 1 or 2, R' is a hydrogen atom or a group chosen among a (C₁-C₃)alkyl group, a halogen atom, a hydroxyl group, a —COOR₁ group, a —NO₂ group, a —NR₁R₂ group, a morpholinyl or a morpholino group, a N-methylpiperazinyl group, a (C₁-C₃)fluoroalkyl group, a (C₁-C₄)alkoxy group and a —CN group, R" is a hydrogen atom or a (C₁-C₄)alkyl group, Z is N or C, Y is N or C, X is N or C, W is N or C, T is N or C, U is N or C, and wherein at most four of the groups V, T, U, Z, Y, X and W are N, and at least one of the groups T, U, Y, X and W is N, or anyone of its pharmaceutically acceptable salts and/or metabolites.

According to another general embodiment, the candidate compounds to be screened are quinoline derivatives selected from any one of the compounds of formula (I):

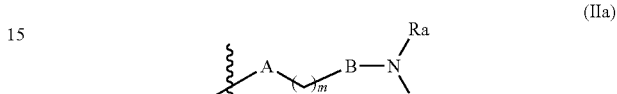
(I)

wherein:

z represents N or C,

means an aromatic ring wherein V is C or N and when V is N, V is in ortho, meta or para of z, i.e. forms respectively a pyridazine, a pyrimidine or a pyrazine group, R independently represent a hydrogen atom, a halogen atom or a group chosen among a —CN group, a hydroxyl group, a —COOR₁ group, a (C₁-C₃)fluoroalkyl group, a (C₁-C₃)fluoroalkoxy group, a (C₃-C₆)cycloalkyl group, a —NO₂ group, a —NR₁R₂ group, a (C₁-C₄)alkoxy group, a phenoxy group, a —NR₁SO₂NR₁R₂ group, a —NR₁SO₂R₁ group, a —NR₁—C(=O)—R₁ group, a —NR₁—C(=O)—NR₁R₂ group, a —SO₂NR₁R₂ group, a —SO₃H group, a —O—SO₂—OR₃ group, a —O—P(=O)—(OR₃)(OR₄) group, a —O—CH₂—COORS group and a (C₁-C₃) alkyl group, said alkyl being optionally mono-substituted by a hydroxyl group, Q is N or O, provided that R" does not exist when Q is O, R₁ and R₂ are independently a hydrogen atom or a (C₁-C₃)alkyl group, R₃ and R₄ independently represent a hydrogen atom, Li⁺, Na⁺, K⁺, N⁺(Ra)₄ or a benzyl group, n is 1, 2 or 3, n' is 1, 2 or 3, R' independently represent a hydrogen atom or a group chosen among a (C₁-C₃)alkyl group, a halogen atom, a hydroxyl group, a —COOR₁ group, a —NO₂ group, a —NR₁R₂ group, a morpholinyl or a morpholino group, a N-methylpiperazinyl group, a (C₁-C₃)fluoroalkyl group, a (C₁-C₄)alkoxy group and a —CN group, and can further be a group chosen among:

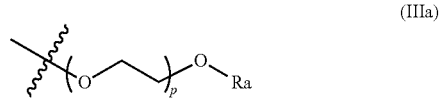
(IIa)

(IIIa)

A is a covalent bond, an oxygen atom or NH,

B is a covalent bond or NH, m is 1, 2, 3, 4 or 5, p is 1, 2 or 3,

Ra and Rb independently represent a hydrogen atom, a (C₁-C₅)alkyl group or a (C₃-C₆)cycloalkyl group, Ra and Rb can further form together with the nitrogen atom to which they are attached a saturated 5- or 6-membered heterocycle optionally containing a further heteroatom chosen among N, O and S, said heterocycle being optionally substituted by one or more Ra, provided that when R' is a group (IIa) or (IIIa), n' may be 2 or 3 only if other R' groups are different from said group (IIa) or (IIIa), R" is a hydrogen atom, a (C₁-C₄)alkyl group or is a group (IIa) as defined above, or anyone of its pharmaceutically acceptable salts and/or metabolites.

The present invention is also directed to the screening of compounds selected from the active metabolites of the herein above defined compounds of formula (I) or anyone of formulae (Ia), (Ib); (Ic), (Id) and (Ie) as defined herein after, more particularly human metabolites, for example N-glucuronide metabolites thereof. In particular, the use of the N-glucuronide or one of its pharmaceutically acceptable salts is also encompassed within the framework of the claimed subject-matter. Said N-glucuronide metabolite (or Compound 1—N glucuronide or "Gluc") has the following formula

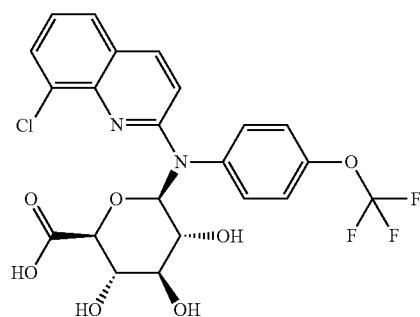 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

It is shown herein that those metabolites demonstrate an anti-viral activity and more particularly an anti-HIV activity. They can be administered and themselves administered as active ingredients.

The N-glucuronide as more particularly described above may be prepared according to the synthetic route as described in patent application EP15305274.

According to a preferred embodiment, Q is N.

According to another preferred embodiment, n is 1 or 2.

According to another preferred embodiment, n' is 1 or 2.

According to another preferred embodiment, R" is a hydrogen atom, a (C$_1$-C$_4$)alkyl group or a group

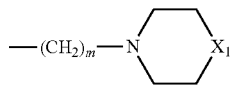

wherein m is 2 or 3 and X$_1$ is O, CH$_2$ or N—CH$_3$.

According to another preferred embodiment, R independently represent a hydrogen atom, a methyl group, a methoxy group, a trifluoromethyl group, a halogen atom and more particularly a fluorine or chlorine atom, a trifluoromethoxy group and an amino group.

According to another preferred embodiment, R' independently represent a hydrogen atom, a halogen atom and more particularly a fluorine or chlorine atom, an amino group, a methyl group or a group

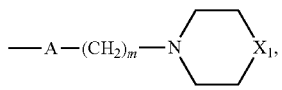

wherein A is O or NH, m is 2 or 3 and X$_1$ is O, CH$_2$ or N—CH$_3$, provided that when R' is such a group, n' is 1 or 2, and when n' is 2, the other R' group is different from said group.

According to one aspect of said preferred embodiment, R' alternatively independently represent a hydrogen atom, a halogen atom and more particularly a fluorine or chlorine atom, a methyl group or a group

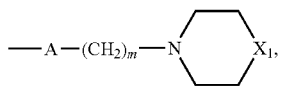

wherein A is O or NH, m is 2 and X$_1$ is O, CH$_2$ or N—CH$_3$, provided that when R' is such a group, n' is 1 or 2, and when n' is 2, the other R' group is different from said group.

All the prior and following particular embodiments may of course be combined together and form part of the invention.

Compounds of formula (I) include compounds of formula (Ia), (Ib), (Ic), (Id) and (Ie), as defined herebelow.

According to a particular embodiment, a quinoline derivative of formula (I) may be a compound of formula (Ia)

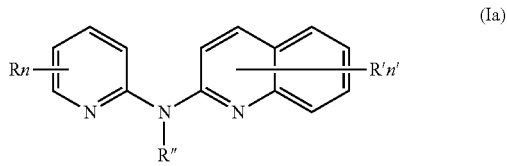

(Ia)

wherein R, R', R", n and n' are as defined above.

According to one aspect of said preferred embodiment, n is 1 or 2.

According to one aspect of said preferred embodiment, n' is 1 or 2.

According to one aspect of said preferred embodiment, R independently represent a hydrogen atom, a halogen atom or a group chosen among a hydroxyl group, a (C$_1$-C$_3$)fluoroalkyl group, a (C$_1$-C$_3$) fluoroalkoxy group, a —NR$_1$R$_2$ group, a (C$_1$-C$_4$)alkoxy group and a (C$_1$-C$_3$)alkyl group.

According to one aspect of said preferred embodiment, R' independently represent a hydrogen atom, a halogen atom or a group chosen among a (C$_1$-C$_3$)alkyl group, a hydroxyl group, a —NR$_1$R$_2$ group, or a group

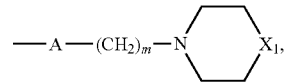

wherein A is O or NH, m is 2 or 3 and X$_1$ is O, CH$_2$ or N—CH$_3$, provided that when R' is such a group, n' is 1 or 2 and when n' is 2, the other R' group is different from said group.

According to one aspect of said preferred embodiment, R" is a hydrogen atom, a (C$_1$-C$_4$)alkyl group or a group

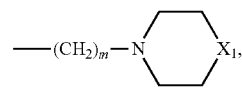

wherein m is 2 or 3 and X$_1$ is O, CH$_2$ or N—CH$_3$, and preferably R" is a hydrogen atom or a methyl group.

According to a particular embodiment, a quinoline derivative of formula (I) may be a compound of formula (Ib)

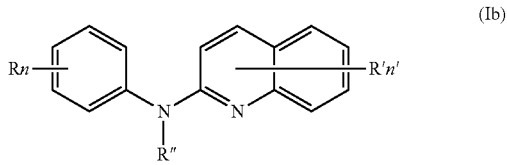

(Ib)

wherein R, R', R", n and n' are as defined above.

According to one aspect of said preferred embodiment, n is 1 or 2.

According to one aspect of said preferred embodiment, n' is 1, 2 or 3.

According to one aspect of said preferred embodiment, R independently represent a hydrogen atom, a halogen atom or a group chosen among a hydroxyl group, a (C$_1$-C$_3$)fluoroalkyl group, a (C$_1$-C$_3$)fluoroalkoxy group, a —NR$_1$R$_2$ group, a (C$_1$-C$_4$)alkoxy group and a (C$_1$-C$_3$)alkyl group.

According to one aspect of said preferred embodiment, R' independently represent a hydrogen atom, a halogen atom or a group chosen among a (C$_1$-C$_3$)alkyl group, a hydroxyl group, a —NR$_1$R$_2$ group, or a group

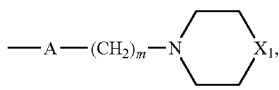

wherein A is O or NH, m is 2 or 3 and X$_1$ is O, CH$_2$ or N—CH$_3$, provided that when R' is such a group, n' is 1 or 2, and when n' is 2, with the other R' group is different from said group.

According to one aspect of said preferred embodiment, R' alternatively independently represent a hydrogen atom, a halogen atom or a group chosen among a (C$_1$-C$_3$)alkyl group, a hydroxyl group or a —NR$_1$R$_2$ group.

According to one aspect of said preferred embodiment, R" is a hydrogen atom, a (C$_1$-C$_4$)alkyl group or a group

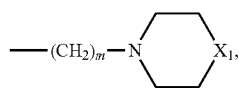

wherein m is 2 or 3 and X$_1$ is O, CH$_2$ or N—CH$_3$, and preferably R" is a hydrogen atom or a methyl group.

According to a particular embodiment, a quinoline derivative of formula (I) may be a compound of formula (Ic)

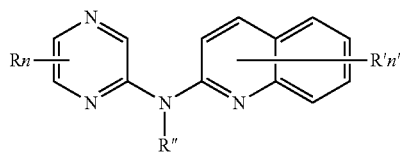

wherein R, R', R", n and n' are as defined above.

According to one aspect of said preferred embodiment, n is 1.

According to one aspect of said preferred embodiment, n' is 1.

According to one aspect of said preferred embodiment, R independently represent a hydrogen atom, a halogen atom or a group chosen among a hydroxyl group, a (C$_1$-C$_3$) fluoroalkyl group, a (C$_1$-C$_3$) fluoroalkoxy group, a —NRiR$_2$ group, a (C$_1$-C$_4$) alkoxy group and a (C$_1$-C$_3$) alkyl group.

According to one aspect of said preferred embodiment, R alternatively independently represent a hydrogen atom or a halogen atom.

According to one aspect of said preferred embodiment, R' independently represent a hydrogen atom, a halogen atom or a group chosen among a (C$_1$-C$_3$) alkyl group, a hydroxyl group, a —NR$_1$R$_2$ group, or a group

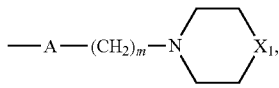

wherein A is O or NH, m is 2 or 3 and X$_1$ is O, CH$_2$ or N—CH$_3$, provided that when R' is such a group, n' is 1 or 2 and when n' is 2, the other R' group is different from said group.

According to one aspect of said preferred embodiment, R' alternatively independently represent a hydrogen atom or a halogen atom.

According to one aspect of said preferred embodiment, R" is a hydrogen atom, a (C$_1$-C$_4$)alkyl group or a group

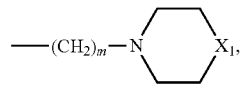

wherein m is 2 or 3 and X$_1$ is O, CH$_2$ or N—CH$_3$, and preferably R" is a hydrogen atom or a methyl group.

According to a particular embodiment, a quinoline derivative of formula (I) may be a compound of formula (Id)

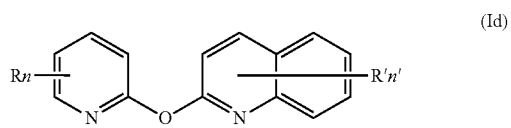

wherein R, R', n and n' are as defined above.

According to one aspect of said preferred embodiment, n is 1.

According to one aspect of said preferred embodiment, n' is 1.

According to one aspect of said preferred embodiment, R independently represent a hydrogen atom, a halogen atom or a group chosen among a hydroxyl group, a (C$_1$-C$_3$)fluoroalkyl group, a (C$_1$-C$_3$)fluoroalkoxy group, a —NR$_1$R$_2$ group, a (C$_1$-C$_4$)alkoxy group and a (C$_1$-C$_3$)alkyl group.

According to one aspect of said preferred embodiment, R alternatively independently represent a hydrogen atom, a (C$_1$-C$_3$)fluoroalkyl group, a (C$_1$-C$_3$)fluoroalkoxy group or a halogen atom.

According to one aspect of said preferred embodiment, R' independently represent a hydrogen atom, a halogen atom or a group chosen among a (C$_1$-C$_3$)alkyl group, a hydroxyl group, a —NR$_1$R$_2$ group, or a group

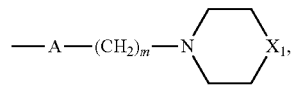

wherein A is O or NH, m is 2 or 3 and X$_1$ is O, CH$_2$ or N—CH$_3$, provided that when R' is such a group, n' is 1 or 2 and when n' is 2, the other R' group is different from said group.

According to one aspect of said preferred embodiment, R' alternatively independently represents a hydrogen atom or a halogen atom.

According to one aspect of said preferred embodiment, R" is a hydrogen atom, a (C$_1$-C$_4$)alkyl group or a group

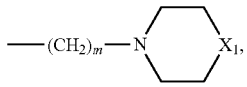

wherein m is 2 or 3 and $X_1$ is O, $CH_2$ or N—$CH_3$, and preferably R" is a hydrogen atom or a methyl group.

According to a particular embodiment, a quinoline derivative of formula (I) may be a compound of formula (Ie)

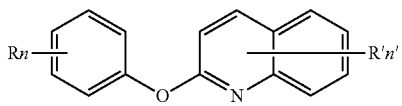

wherein R, R', n and n' are as defined above.

According to one aspect of said preferred embodiment, n is 1.

According to one aspect of said preferred embodiment, n' is 1.

According to one aspect of said preferred embodiment, R independently represent a hydrogen atom, a halogen atom or a group chosen among a hydroxyl group, a ($C_1$-$C_3$)fluoroalkyl group, a ($C_1$-$C_3$)fluoroalkoxy group, a —$NR_1R_2$ group, a ($C_1$-$C_4$)alkoxy group and a ($C_1$-$C_3$)alkyl group.

According to one aspect of said preferred embodiment, R alternatively independently represent a hydrogen atom, a ($C_1$-$C_3$)fluoroalkyl group, a ($C_1$-$C_3$)fluoroalkoxy group or a halogen atom.

According to one aspect of said preferred embodiment, R' independently represent a hydrogen atom, a halogen atom or a group chosen among a ($C_1$-$C_3$)alkyl group, a hydroxyl group, a —$NR_1R_2$ group, or a group

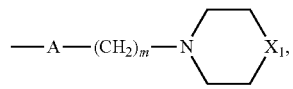

wherein A is O or NH, m is 2 or 3 and $X_1$ is O, $CH_2$ or N—$CH_3$, provided that when R' is such a group, n' is 1 or 2 and when n' is 2, the other R' group is different from said group.

According to one aspect of said preferred embodiment, R' alternatively independently represent a hydrogen atom or a halogen atom.

According to one aspect of said preferred embodiment, R" is a hydrogen atom, a ($C_1$-$C_4$)alkyl group or a group

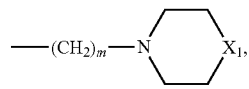

wherein m is 2 or 3 and $X_1$ is O, $CH_2$ or N—$CH_3$, and preferably R" is a hydrogen atom or a methyl group.

The compounds of the invention may exist in the form of free bases or of addition salts with pharmaceutically acceptable acids.

Suitable physiologically acceptable acid addition salts of compounds of formula (I) include hydrobromide, tartrate, citrate, trifluoroacetate, ascorbate, hydrochloride, tartrate, triflate, maleate, mesylate, formate, acetate and fumarate.

The compounds of formula (I) and or salts thereof may form solvates or hydrates and the invention includes all such solvates and hydrates.

The terms "hydrates" and "solvates" simply mean that the compounds (I) according to the invention can be in the form of a hydrate or solvate, i.e. combined or associated with one or more water or solvent molecules. This is only a chemical characteristic of such compounds, which can be applied for all organic compounds of this type.

The compounds of formula (I) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

In the context of the present invention, the term:
"halogen" is understood to mean chlorine, fluorine, bromine, or iodine, and in particular denotes chlorine, fluorine or bromine,
"($C_1$-$C_5$)alkyl" as used herein respectively refers to $C_1$-$C_5$ normal, secondary or tertiary saturated hydrocarbon. Examples are, but are not limited to, methyl, ethyl, 1-propyl, 2-propyl, butyl, pentyl,
"($C_3$-$C_6$)cycloalkyl" as used herein respectively refers to cyclic saturated hydrocarbon. Examples are, but are not limited to cyclopropyl, cyclobutyl, cyclopentyl, cyclohexyl,
"($C_1$-$C_4$)alkoxy" as used herein respectively refers to O—($C_1$-$C_4$)alkyl moiety, wherein alkyl is as defined above. Examples are, but are not limited to, methoxy, ethoxy, 1-propoxy, 2-propoxy, butoxy,
"fluoroalkyl group" and "fluoroalkoxy group" refers respectively to alkyl group and alkoxy group as above-defined, said groups being substituted by at least one fluorine atom. Examples are perfluoroalkyl groups, such as trifluoromethyl or perfluoropropyl,
"saturated 5- or 6-membered heterocycle" as used herein respectively refers to a saturated cycle comprising at least one heteroatom. Examples are, but are not limited to, morpholine, piperazine, thiomorpholine, piperidine and pyrrolidine.

EXAMPLES

Example 1: Compound 1 Directly Interacts with the CBC Complex and Promotes the Interaction of CBP20 with CBP80

1. Material & Methods
A. Preparation the Recombinant CBC Complex for In Vitro Studies.

The recombinant CBC complex, comprising CBP20 and CBP80, is prepared according to the protocol which has been described in Worch, R. et al. (Specificity of recognition of mRNA 5' cap by human nuclear cap-binding complex. RNA 11, 1355-1363 (2005)).

B. Induction of Dose-Dependent Covalent Bridging with the CBC Complex.

Compound 1 can make covalent binding with purified CBC complex after 15 min irradiation with UV light at 365 nm.

C. Gel-Mobility Shift Assay

Gel-mobility shift assay in the presence of a m(7)GpppG cap analogue has been established according to the protocol described in Mazza et al. (Large-scale induced fit recognition of an m(7)GpppG cap analogue by the human nuclear cap-binding complex. EMBO J. 21, 5548-5557 (2002)).

D. Limited Proteolysis on the CBC Complex.

Limited proteolysis of the CBC complex has been established according to the protocol described in Mazza et al. (Large-scale induced fit recognition of an m(7)GpppG cap analogue by the human nuclear cap-binding complex. EMBO J. 21, 5548-5557 (2002)).

E. Mass-Spectrometry Analysis.

Mass-spectrometry analysis of the CBC complex has been established according to the protocol described in Schirle et al. (Mass spectrometry-based proteomics in preclinical drug discovery. Chem Biol., 19:72-84 (2012)).

Proteins were separated on SDS-PAGE gels (4-15% polyacrylamide, Mini-PROTEAN® TGX™ Precast Gels, Bio-Rad, Hercules USA) and stained with Page Blue Stain (Fermentas). Gel lanes were cut into 3 gel pieces and destained with three washes in 50% acetonitrile and 50 mM TEABC (TriEthylAmmonium BiCarbonate). After protein reduction (with 10 mM dithiothreitol in 50 mM TEABC at 56° C. for 45 min) and alkylation (55 mM iodoacetamide TEABC at room temperature for 30 min) proteins were digested in-gel using trypsin (1 µg/band, Gold, Promega, Madison USA) as previously described in Shevchenko et al. (Mass spectrometric sequencing of proteins silver-stained polyacrylamide gels. Anal. Chem. 1996, 68 (5), 850-8; 1996). Digested products were dehydrated in a vacuum centrifuge and reduced to 4 µL.

Generated peptides were analyzed on-line using nanoflow HPLC-nano-electrospray ionization on a Q-Exactive mass spectrometer (ThermoScientific, Waltham USA) coupled with an Ultimate 3000 RSLC apparatus (Thermo Fisher Scientific). Desalting and pre-concentration of the samples were performed on-line on a Pepmap® precolumn (0.3 mm×10 mm). A gradient consisting of 0-55% B for 35 min and 90% B for 10 min (A=0.1% formic acid in water; B=0.1% formic acid, 80% acetonitrile in water) at 300 nl/min was used to elute peptides from the capillary (0.075 mm×150 mm) reverse-phase column (Acclaim PepMap® RSLC, Thermo Fisher Scientific), fitted with an uncoated silica PicoTip Emitter (NewOjective, Woburn, USA). Eluted peptides were electrosprayed online at a voltage of 1.9 kV into an Q-Exactive mass spectrometer. MS spectra (m/z, 400-2,000) were acquired using the Xcalibur software (v 3.0, Thermo Fisher Scientific) in the positive ion mode with a resolution of 70,000 for the precursor ion scan. For all full scan measurements with the Orbitrap detector a lock-mass ion from ambient air (m/z 445.120024) was used as an internal calibrant as described in Olsen et al. (Parts per million mass accuracy on an Orbitrap mass spectrometer via lock mass injection into a C-trap. Mol. Cell. Proteomics 4, 2010-2021; 2005). MS/MS spectra were acquired in the Data-Dependent Acquisition mode, in which the TOP10 most abundant precursor ions with maximum integration time of 250 ms and a target value of $3*10^6$ ions. Peptide fragmentation was performed via higher-energy collisional dissociation set at 26 V of normalized collisional energy. The MS/MS spectra were acquired at a resolution of 17,500, with a target value of $1*10^5$ ions and a maximum integration time of 120 ms.

All MS/MS spectra were searched against the *Homo sapiens* CPS database (85,895 sequences and specific sequences of CBP80-CBC20, release september 2014, http://www.uniprot.org/) by using the Proteome Discoverer software v1.4 (Thermo Fisher Scientific) and Mascot v2.5 algorithm (http://www.matrixscience.com/) with trypsin enzyme specificity and one trypsin missed cleavage. Carbamidomethylation was set as fixed cystein modification and oxidation was set as variable methionine modification for searches. Mass tolerances in MS and MS/MS were set to 5 ppm and 0.5 Da respectively. Management and validation of mass spectrometry data were performed using the Proteome Discoverer software (Mascot significance threshold p<0.05, with a minimum of one peptide per protein).

In addition to protein/peptide identifications, the Skyline software v2.6. (http://proteome.gs.washington.edu/software/skyline) was used to process ion intensity chromatograms of specific peptides from full-scan mass spectral data (MS1) acquired during HPLC MS/MS proteomic experiments, as described in MacLean et al. (Effect of collision energy optimization on the measurement of peptides by selected reaction monitoring (SRM) mass spectrometry. Anal Chem 82, 10116-10124; 2010).

F. Quantification of the Binding of the CBC Complex to an m(7)GpppG Cap Analogue.

Recombinant human CBC was incubated with a capped RNA substrate and analyzed by native gel electrophoresis in order to resolve the different RNA and RNA-protein complexes according to Mazza et al. (Large-scale induced fit recognition of an m(7)GpppG cap analogue by the human nuclear cap-binding complex. EMBO J. 21, 5548-5557 (2002).

2. Results

Figure 3:
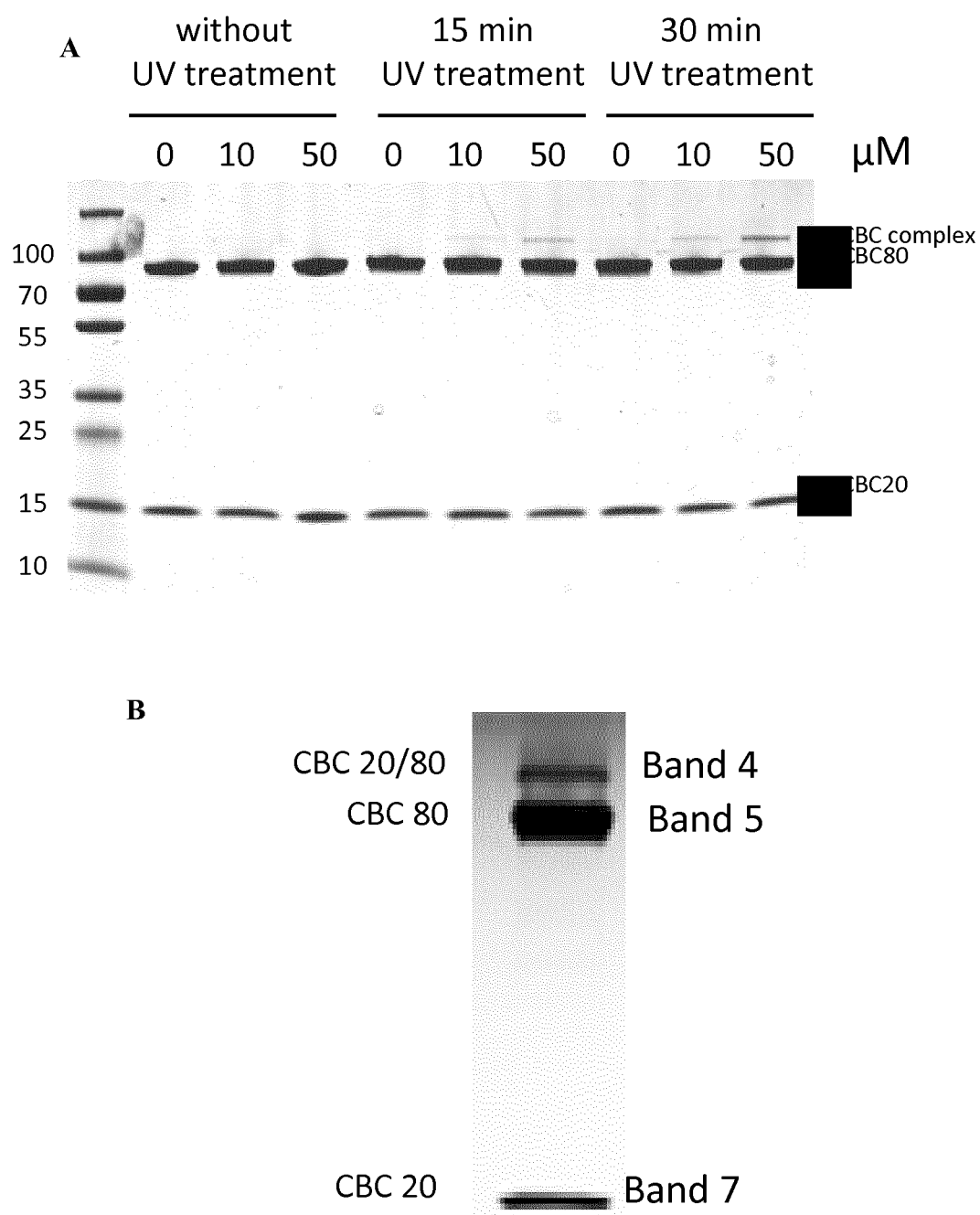
FIG. 3. Compound 1 promotes the interaction of CBP20 with CBP80. A) Purified recombinant CBP20 and CBP80 proteins were incubated with the indicated concentrations of Compound 1-N-glucuronide and they were either untreated (lanes 1-3), treated during 15 min (lanes 4-6) or 30 min (lanes 7-9) with UV light. Proteins were analyzed by SDS-PAGE and stained with Coomassie blue. Compound 1 and Compound 1-N-glucuronide promote UV crosslinking of CBP20 and CBP80. B) Recombinant human CBC was incubated with Compound 1-N-glucuronide and treated with UV for 15 min. After crosslinking the proteins were resolved in SDS-PAGE and stained with Coomassie blue (left panel). Stained proteins (Band 4, Band 5 and Band 7) were digested with trypsin and analysed by mass spectrometry.

Using a derivative of Compound 1 that has a photoactivatable moiety and competition with Compound 1 on purified recombinant CBP20 and CBP80 (CBC), it was discovered that Compound 1, itself, is able to induce dose-dependent covalent bridging between CBP20 and CBP80, after UV irradiation and this complex can be resolved by SDS-PAGE (FIGS. 2 and 3).

Mass spectrometry analysis of gel purified CBP20, CBP80 and the CBC complex (80 and 20), showed that the trypsin digestion of CBC (CBP80 and CBP20) complex gave rise to all predicted peptides except the peptide at the position 37-66 of CBP20 which was reproducibly under-represented or absent. However, individual digestion with trypsin of either CBP20 or CBP80 from the same sample gave rise to all predicted peptides. Remarkably, the peptide 37-66 in the crystal structure of the CBC (Mazza et al.; Crystal structure of the human nuclear cap binding complex. Mol. Cell 8, 383-396 (2001)) corresponds to the interface between CBP20 and CBP80, which could encompass one site of interaction between Compound 1 and the CBC complex (FIG. 3).

Figure 4:
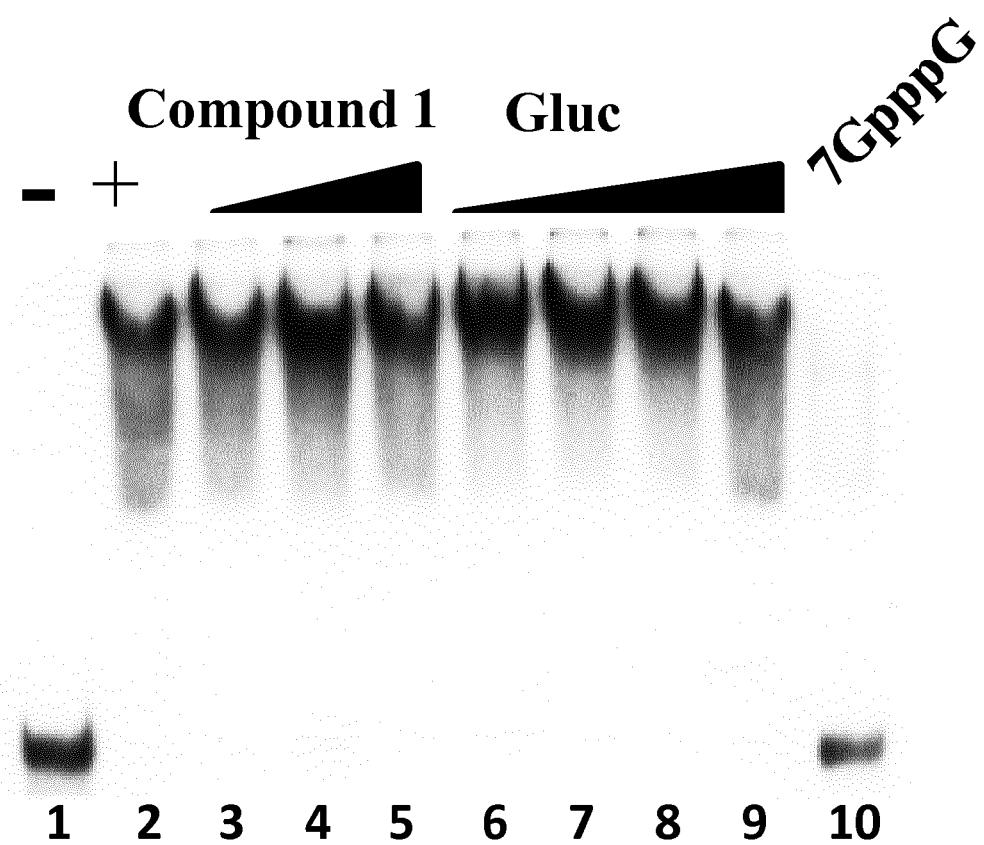
FIG. 4. Unlike m7GpppG cap structure, neither Compound 1 nor Compound 1-N-glucuronide interfere with the binding of capped RNA to the CBC complex. Recombinant human CBC was incubated with a capped RNA substrate and analyzed by native gel electrophoresis in order to resolve the different RNA and RNA-protein complexes: free RNA (lane 1), and CBC-RNA complexes (lanes 2-10) in the presence of 12 mM of m7GppG (lanes 10) or 5 µM, 10 µM or 50 µM of Compound 1 (lanes 2-4, respectively) or 5 µM, 10 µM, 50 µM or 100 µM of Compound 1-N-glucuronide (lanes 5-9, respectively).

However, Compound 1 does not affect the binding of CBC complex to capped RNA probe in a gel mobility shift assay. While the complex between CBC and capped RNA was competed by the $m^7$GpppG, no competition was observed with Compound 1 at any concentration tested, confirming that Compound 1 does not interact with the cap binding site of CBP20 (FIG. 4).

These results thus fully support the use of CBP20, CBP80, and of the complex CBP20/CBP80 as a method for screening compounds efficient for treating or preventing a viral infection or virus-related condition in an individual.

These results also support that Compound 1 binds directly to the CBC complex but does not interfere with cap binding nor export of bulk pol II transcripts.

Example 2: Potency of Compound 1 to Inhibit HIV-1 Production in PBMC- and Macrophages-Infected Cells 1. Material & Methods A. Cell Culture and Infection Buffy coats from HIV-negative individuals were obtained from the local blood donation center in Zurich, Switzerland (http://www.blutspendezurich.ch/) and Centre de transfusion sanguine Montpellier. Human peripheral blood mononuclear cells (PBMCs) were isolated by Ficoll (Axis-Shield PoC AS) gradient centrifugation. The cells have then been cultivated at 37° C., 5% CO2 to a density of 1×106 cells/mL in RPMI Glutamax medium (Life Technologies Ref 61870-010) supplemented with 10% fetal calf serum (FCS) (Thermo Fischer Ref SV30160.03), 1000 U/mL of IL2 (Peprotech Ref 200-02) and 5 µg/mL of PHA (Roche Ref 1249738) for activation. Three days later, cells have been pooled and resuspended to a density of 1×106 cells/mL in RPMI Glutamax medium supplemented with 10% fetal calf serum (FCS) 1000 U/mL of IL-2 for infection. HIV-1 infection has been performed with 10 µg of Ada-M $R_5$ HIV strain per mL of cells for 4 hours. Cells were then centrifuged and resuspended to a density of 1×106 cells/mL in medium supplemented with diluted DMSO solubilized drug (Sigma Ref D4818) according to a final 0.05% DMSO concentration. Cells were treated for 6 days with a partial medium change at day 3. Cell culture supernatant HIV p24 titration was performed by ELISA with Ingen Innotest kit (Ingen Ref 80564) according to manufacturer's instructions.

To generate monocyte derived macrophages (MDMs), monocytes were isolated using CD14 microbeads (catalog no. 130-050-201; Miltenyi) and cultured in X-VIVO10 medium (Lonza) supplemented with GM-CSF 1000 U/ml and M-CSF 100 ng/ml for 6 days. Monocytes were seeded at a cell count of 50'000 cells per well in a 96 well plate. After 6 days medium was replaced with X-VIVO10 w/o Cytokines. After 2 days Macrophages were treated with Compound 1 o/n and next day infected with Yu-2 virus for 6 hrs, washed with PBS and cultured in medium containing the compounds for 12 days. Supernatant for p24 Elisa was collected 2 times a week.

HeLa cells from ATCC have been cultivated at 37° C., 5% CO2 in DMEM Glutamax medium (Life Technologies Ref 31966-021) supplemented with 10% fetal calf serum (FCS) (Thermo Fischer Ref SV30160.03). pΔPSP (2 µg per 400.000 cells) transient transfection was performed by Jet-PEI reagent (PolyPlus Ref 101-10N) according to manufacturer's instruction.

B. Monitoring of p24 Antigen Levels.

Cells were treated with 0.01 µM up to 30 µM and p24 antigen levels were monitored in culture supernatant over a 12 day period. Cell culture supernatant HIV p24 titration was performed by ELISA with Ingen Innotest kit (Ingen Ref 80564) according to the manufacturer's instructions.

2. Results

The first functional screening of the new compounds was based on the use of freshly isolated human peripheral blood mononuclear cells (PBMCs) from healthy donors. These PBMCs were infected by the laboratory HIV strain Ada-MR5.

FIG. 5 shows dose dependent inhibition of HIV-1 replication in stimulated PBMCs from 7 different donors. Interestingly, treatment with Compound 1 did not alter the different populations of lymphocytes present in PBMCs.

To generalize the effect of Compound 1 on HIV-1 replication in other primary cells, the same protocol was repeated using infected macrophages, which act as viral reservoirs. Cells were treated with 0.01 µM up to 30 µM and p24 antigen levels were monitored in culture supernatant over a 12 day period (FIG. 5). Interestingly, Compound 1 blocked virus replication efficiently and in a dose dependent manner reaching inhibition levels of up to 90% in primary macrophages at 0.1 µM. However, cell viability was not decreased under Compound 1 treatment (data not shown).

These results provide evidence that the screening method is suitable or selecting compounds having low toxicity, but which remain suitable for inhibiting HIV-1 replication, in PBMCs and macrophages.

Since the previous experiments were all performed with primary human cells infected with macrophage-tropic (R5) strains (Ada-MR5 and YU2), it was shifted to an in vitro system that may be more relevant to the clinical situation since it involves infecting primary cells with HIV-1 isolates from patients. As shown in FIG. 6, Compound 1 had a strong inhibitory effect for all HIV-1 subtypes tested including subtype B, C and recombinant viruses. In particular, Compound 1 very efficiently inhibits the replication of viral strains harbouring mutations that confer resistance to different therapeutic agents in vitro, and there were no resistance-inducing mutations detected after treatment with Compound 1 for at least 24 weeks.

These results provide evidence that the screened compounds do not select for HIV specific mutations and are not genotoxic.

Example 3: Efficacy of Compound 1 to Inhibit Viral Replication in Humanized Mice 1. Material & Methods A. Generation of Humanized Mouse Models SCID mice were reconstituted with fresh human PBL for two weeks and the reconstitution rates were estimated by human IgG titration according to Denton et al. (Humanized mouse models of HIV infection. AIDS Rev 13, 135-148 (2011)) and Berges et al. (The utility of the new generation of humanized mice to study HIV-1 infection: transmission, prevention, pathogenesis, and treatment. Retrovirology 8, 65 (2011)).

Reconstituted SCID mice were infected with JRCSF HIV-1 strain by intraperitoneal injection. Control group received by gavage labrafil and 5% DMSO (n=15) and treated group 20 mg/kg b.i.d of Compound 1 in labrafil and 5% DMSO (n=14) for 15 days.

NOD.scid.IL2R −/− (NSG) mice were bred and maintained in individual ventilated cages and were fed autoclaved food and water. Mice with a human immune system (NSG-HIS) were generated as described in Nischang et al. (Humanized mice recapitulate key features of HIV-1 infection: a novel concept using long-acting anti-retroviral drugs for treating HIV-1. PLoS ONE 7, e38853 (2012).

Briefly, newborn (<5 days old) NSG mice received sublethal (1 Gy) total body irradiation with a Cs source, and then received 2×105 transduced or untransduced CD34+ human HSCs using a 50 µl Hamilton syringe via the intrahepatic (i.h.) route. All manipulations of NSG-HIS mice were performed under laminar flow. Gavage of mice was performed daily with a stainless steel gavage needle (Straight 22 Gauge, 1.4 inch in length). Compound 1 was dissolved in DMSO (Sigma), and then diluted to 5% or less according to the dose required in a suitable vehicle (Labrafil M 1944 CS; COOPER INDUSTRIE, Place Lucien Auvert 77020 MELUN CEDEX 20). Mice did not receive more than 150 µl in volume per day. Mice were monitored three times a week for symptoms or signs of adverse events, according to a standard score sheet.

B. HIV Virus Stock and Infection of Mice

Viral stocks were obtained by polyethylenimine (PEI)-mediated transfection (Polysciences) of 293T cells with a pYU-2 (R5 tropic) plasmid provided through the NIH AIDS Research and Reference Reagent Program. 48 hours after transfection, the virus was harvested, filtered (0.45 µm), and frozen at −80° C. Viral titers were determined as described in McDougal et al. (Immunoassay for the detection and quantitation of infectious human retrovirus, lymphadenopathy-associated virus (LAV). J. Immunol. Methods 76, 171-183 (1985)).

Briefly, TCID50 (tissue culture infectious dose 50%) was determined by infecting human CD8+ T-cell-depleted peripheral blood mononuclear cells (PBMCs) from three donors which were stimulated by addition of IL-2, PHA and anti-CD3 beads (Dynal 11131D, Life Technologies). Then, viral stocks were adjusted to 1×106 TCID50/ml, aliquoted and frozen at −80° C. before use. Mice were infected intraperitoneally i.p. with HIV YU-2, 1×106 TCID50 per mouse. HIV RNA plasma levels were measured by RT-PCR (AmpliPrep/COBAS TaqMan HIV-1 Test, Roche) at various times after infection.

C. Flow Cytometry

Cell suspensions were labeled with anti-human monoclonal antibodies (mAb) targeting the following cell-surface markers: CD45-FITC, CD3-PE, CD4-Pe Cy7, CD8-BV421 and CD19-APC (all from Biolegend). Washing and reagent dilutions were done with FACS buffer (PBS containing 2% fetal calf serum and 0.05% sodium azide (NaN3). All acquisitions were performed on a Cyan ADP (Beckman Coulter) flow cytometer. Data were analyzed with FlowJo software (Ashland, Oreg.). Cellular debris and dead cells were excluded by their light-scattering characteristics.

2. Results

Humanized mice reconstituted with human lymphoid cells, provide rapid, reliable, reproducible experimental systems for testing the efficacy of Compound 1 in vivo 32,33. In the initial setting, SCID mice were reconstituted with PBMCs and then infected with the HIV-1 strain JR-CSF 33,34. Mice were treated by oral gavage with Compound 1 at a dose-level of 20 mg/kg twice a day for 15 days. Measures of viral RNA showed that oral treatment with Compound 1 was able to significantly reduce the viral load over a period of 15 days of treatment (FIG. 7A). FACS analysis of blood samples showed that treatment with Compound 1 prevents depletion of CD4+ cells following infection of reconstituted mice and thereby restores CD8+/CD4+ ratio back to that of non-infected mice (FIG. 7B).

Figure 7C:
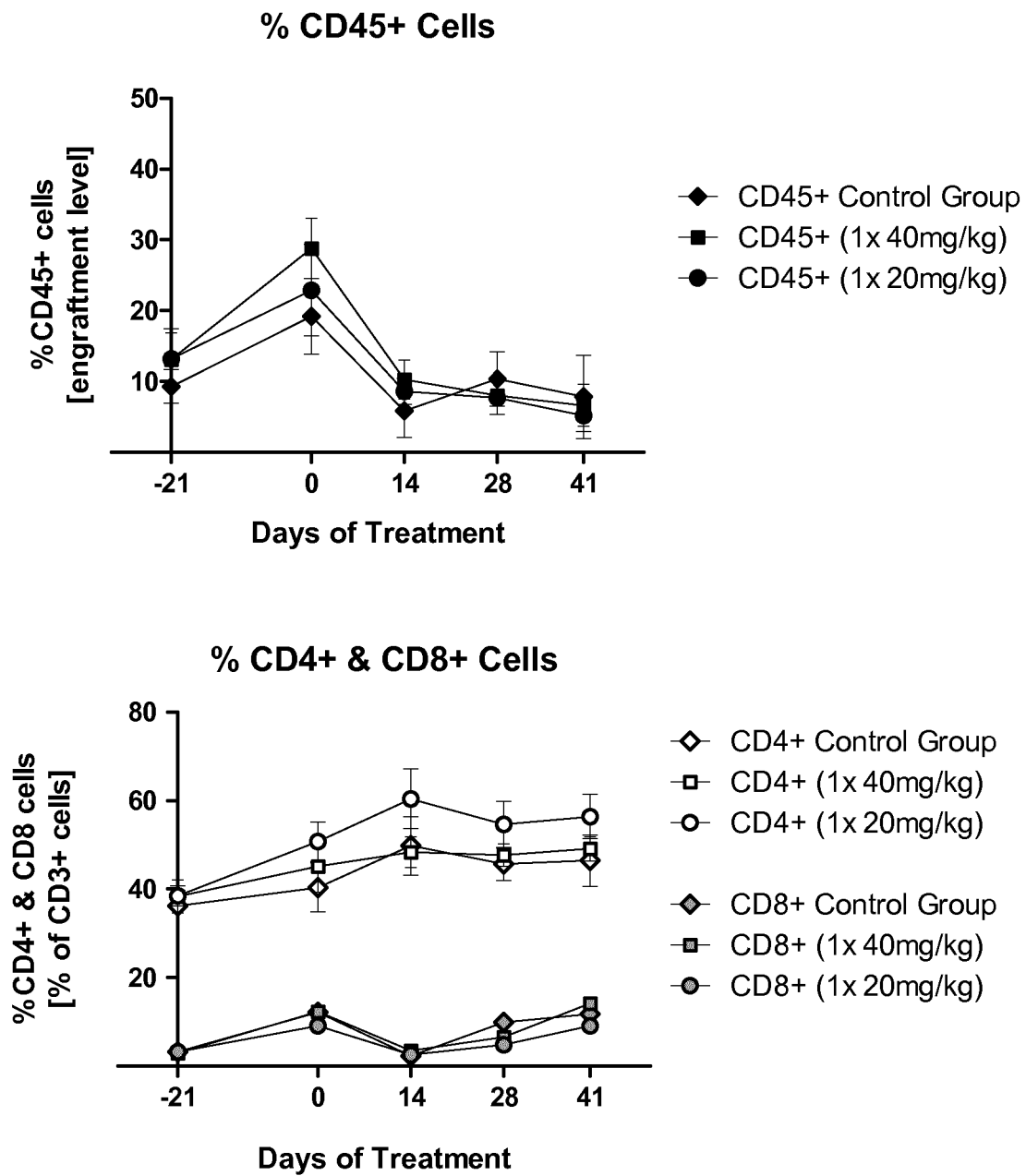
FIG. 7. Efficacy of Compound 1 to inhibit viral replication in humanized mice. A) Reconstituted SCID mice were infected with JRCSF HIV-1 strain by intraperitoneal injection. Control group received by gavage labrafil and 5% DMSO (n=15) and treated group 20 mg/kg b.i.d of Compound 1 in labrafil and 5% DMSO (n=14) for 15 days. Two independent experiments were performed with 5 and 10 reconstituted mice for each group. Viral load was assessed by measuring viral RNA using the Amplicor HIV-1 Monitor from Roche. B) FACS analysis was performed on peritoneal wash at day 15 post-treatment to assess the CD8/CD4 ratio. C) Engrafted NSG humanized mice were treated by oral gavage with Compound 1 at either 20 mg or 40 mg/kg once a day for 30 days and indicated lymphocyte populations (CD45+; CD4+ and CD8+) were monitored by FACS analysis. D) NSG humanized mice were infected with the YU2 HIV-1 virus and treated either by oral gavage with Compound 1 at 40 mg/kg once a day for 30 days or by HAART (3TC-Tenofovir-Raltegravir and AZT). For HAART, food pellets were made by mixing 2.5 g of 3TC, TDF and AZT each, and 5 g of RTV with 5 kg of ground protein-rich, vitamin-fortified food (Nafag 3432, Provimi Kliba AG, Switzerland) which was subsequently formed to food pellets and sterilized by gamma-irradiation with 25 kGy. Viral load was assessed by measuring viral RNA using the Amplicor HIV-1 Monitor from Roche.
Figure 7D:
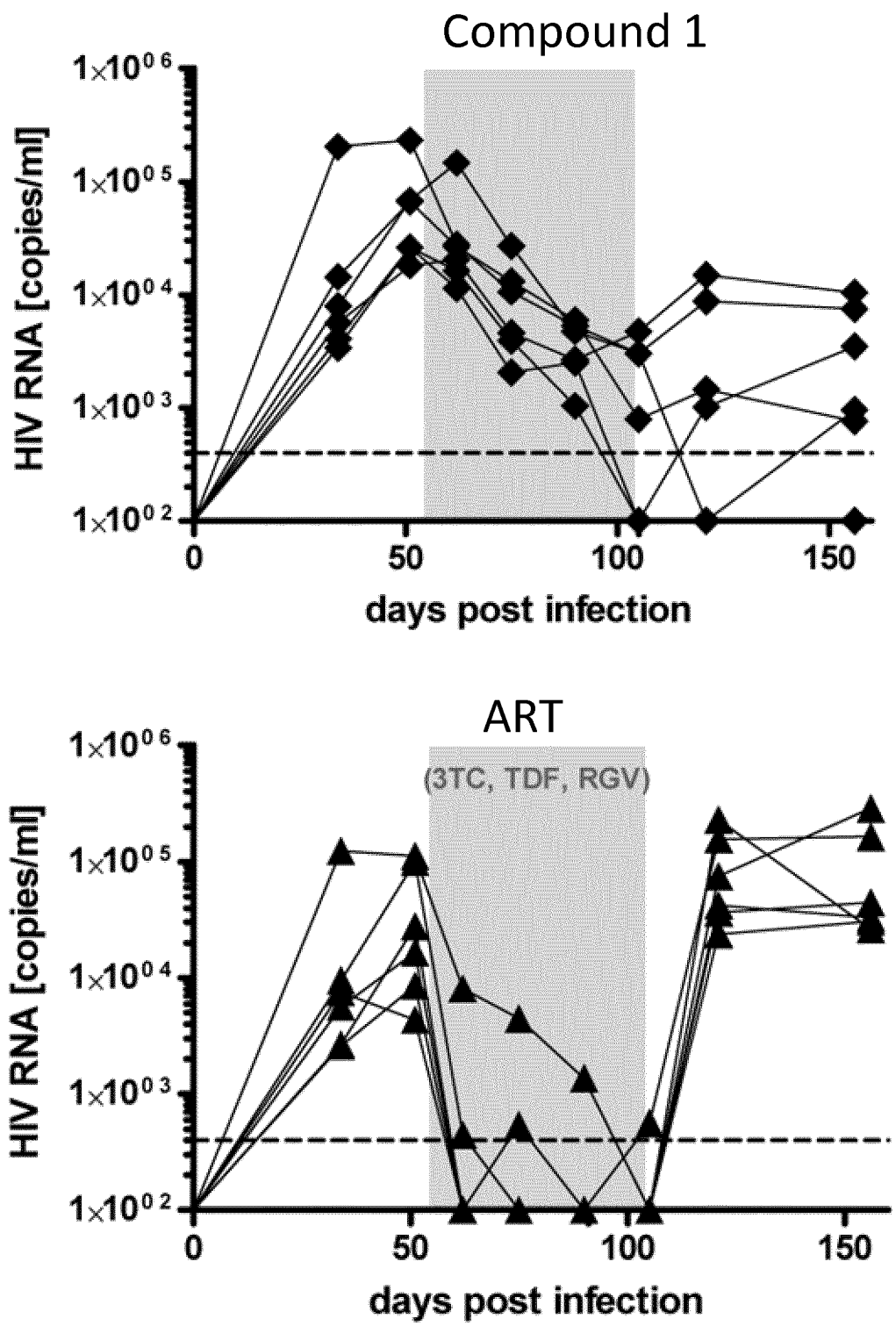

To test the long term effect of Compound 1 on the immune system and viral replication in infected hu mice, newborn NOG mice were transplanted with CD34+ haematopoietic progenitor cells isolated from umbilical cord blood (see Nischang et al.; Humanized mice recapitulate key features of HIV-1 infection: a novel concept using long-acting anti-retroviral drugs for treating HIV-1. PLoS ONE 7, e38853; 2012). This hu mouse model has previously been shown to be valuable for exploring the antiviral potency of new compounds targeting the latent HIV reservoirs 35. Treatment of NOG hu mice for one month with 20 mg/kg or 40 mg/kg of Compound 1 neither alters engraftment values of CD45+ cells nor the ratio of CD8+/CD4+ compared to controls without treatment (FIG. 7C). In this study NOG hu mice were infected with the YU2 HIV-1 virus and fed daily for 30 days with 40 mg/kg of Compound 1 or with HAART (3TC-Tenofovir-Raltegravir and AZT) and viral loads were measured as before. Compound 1 reduced the viral load over a period of 30 days of treatment but more importantly, the viral load remained low for at least 50 days after treatment termination (FIG. 7D). In contrast, rebound up to levels comparable to the initial infection was seen in the HAART group (FIG. 7D).

Thus these results show that the screened Compound 1 is the first robust anti-HIV drug able to suppress viral load sustainably after treatment arrest.

Example 4: Compound 1 Influences REV-Mediated HIV RNA Biogenesis and Export

1. Material & Methods

A. Cell Culture & Infection

Hela 128*MS2-GFP cells (kind gift from E. Bertrand, IGMM Montpellier, France) were maintained in DMEM Glutamax medium (Life Technologies Ref 31966-021) containing 10% fetal bovine serum (Hyclone), penicillin/streptomycin (10 U/ml) in a humidified 5% CO2 incubator at 37° C. Cells were transfected with pSG-FlagRev plasmid (kind gift from P. Jalinot, ENS Lyon, France) for 24 hours with JetPEI reagent (PolyPlus Ref 101-10N) according to manufacturer's instruction.

B. Immunofluorescence Analysis

Cells plated on cover slips were fixed for 10 min in 3.7% formaldehyde (in PBS) followed by a 2-min permeabilization with 0.1% Triton X-100 (in PBS) and incubation in PBS containing 0.1% bovine serum albumin. Rev protein was revealed using antibody against HIV-1 Rev protein (Santa Cruz) and nuclei were stained using Hoechst 33342 (Sigma-Aldrich). Cells were washed in PBS mounted with DAKO mounting medium and observed under the fluorescence microscope.

Cell imaging was performed with a Leica DM6000 (Leica, Wetzlae, Germany) with PL APO grade oil×63 objective. Images were captured with a Coolsnap HQ2 camera (Roper Scientific Inc.) driven by Metamorph (Molecular Devices) and processed using Fiji software and GFP fluorenscence intensity was determined using the measure module of Fiji.

2. Results

To test the effect of Compound 1 on splicing and/or export of viral RNA, used an HIV reporter stem system was used to visualize single HIV RNA molecules in living cells. It is based on an HIV reporter system containing the 5' and 3' LTRs that harbour the promoter and polyA sites, respectively, packaging sequences and RRE elements, in addition to 128 MS2 binding sites that were inserted between the major donor HIV-1 site (SD1) and the last splice acceptor (SA7) (See FIG. 8a).

The reporter was introduced in HeLa cells stably expressing Tat and MS2-GFP, using the Flp-In system to create cells carrying single copy transgene. Stable expression of MS2-GFP protein allowed excellent visualisation of the transcription site and single pre mRNA molecules (FIG. 8b) and did not alter splicing rate (data not shown).

Figure 8B:
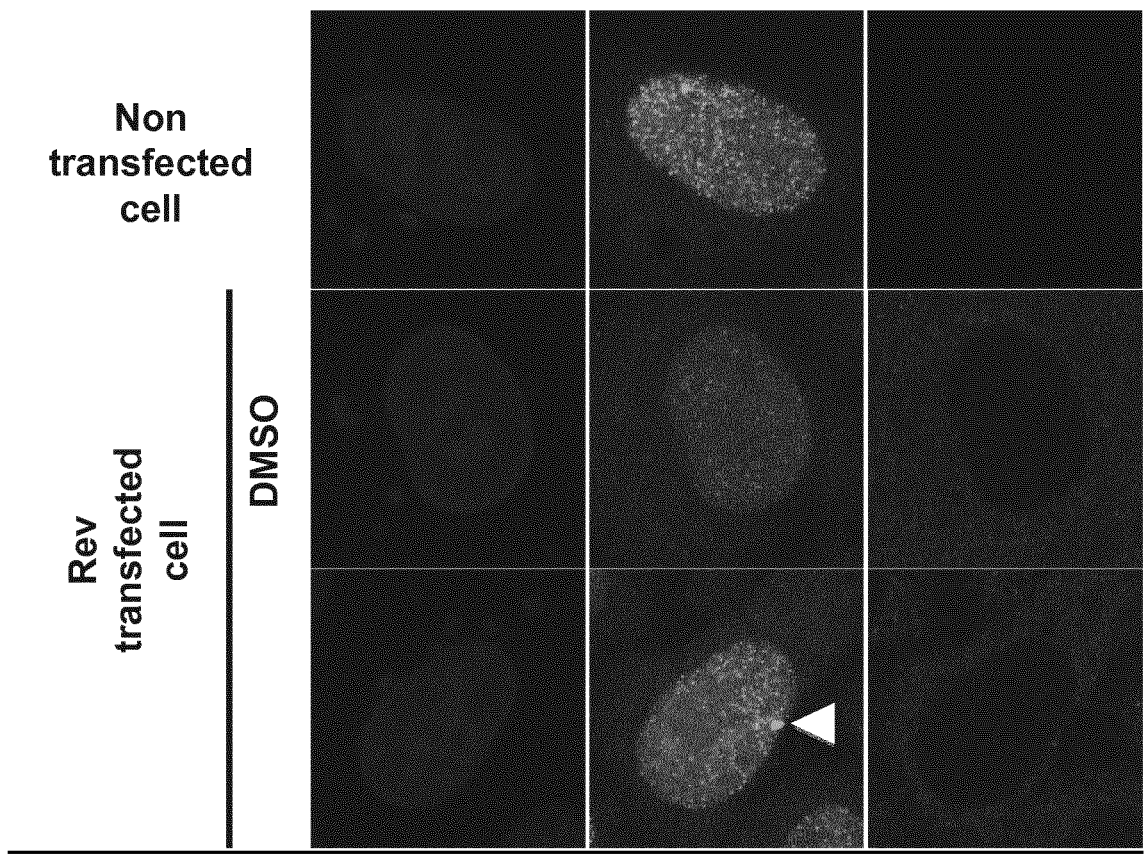
Figure 8C:
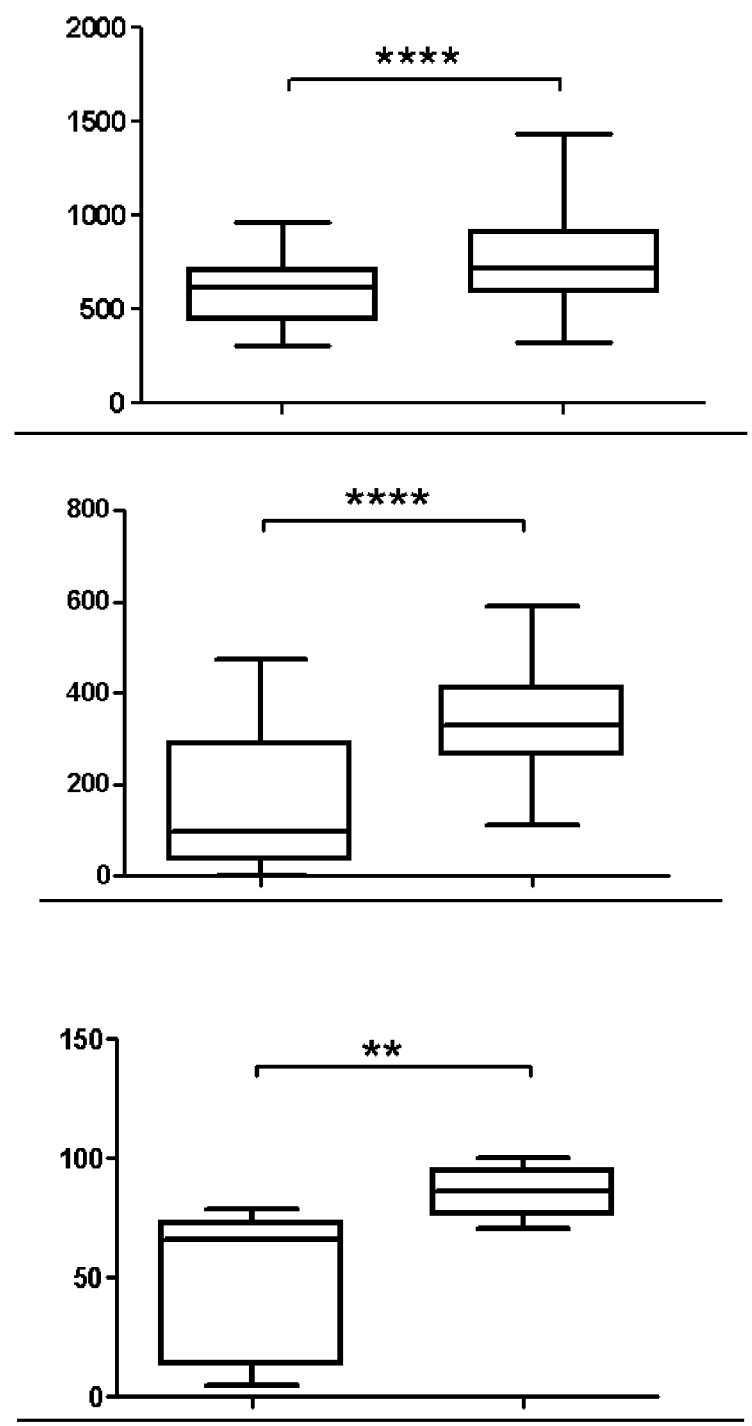

To assay for RNA export, these cells were transfected with constructs expressing Rev protein that will bind to the RRE and facilitate the export of unspliced viral RNA, while protecting it from the splicing machinery. Rev expression led to a reduced GFP signal at both the transcription site and the nucleoplasm (FIG. 8b). This result is expected since following association of Rev with the high-affinity RRE "nucleation site", additional Rev molecules can polymerize along the length of the RRE in a step-wise fashion through both protein-protein and protein-RNA interactions, thereby removing MS2-GFP from their target sequences.

Rev-mediated RNA export leads to a reduction of unspliced RNA in the nucleus and the intensity of GFP in the nucleus. Crucially, Compound 1 interferes with both activities of Rev by preserving the GFP signal both at the transcription site and in the nucleoplasm of cells expressing Rev (FIGS. 8b and c). However, Compound 1 shows no effect on reporter cells in the absence of Rev (Data not shown).

Thus, these results show that the screened Compound 1 prevents specifically Rev-mediated export of viral RNA.

Example 5: Compound 1 Increases the Levels of Spliced HIV RNA

1. Material & Methods

Quantification of Viral and Non-Viral RNA Splicing

Quantification of viral RNA splicing is achieved using the protocols detailed in Bakkour et al. (Small-molecule inhibition of HIV pre-mRNA splicing as a novel antiretroviral therapy to overcome drug resistance. PLoS Pathog. 3, 1530-1539 (2007).

Quantification of non-viral RNA splicing is achieved using the protocols detailed in Klinck et al. (Multiple alternative splicing markers for ovarian cancer. Cancer Res. 68, 657-663 (2008)) and Venables et al. (Cancer-associated regulation of alternative splicing. Nat. Struct. Mol. Biol. 16, 670-676 (2009)).

Other protocols are as described previously.

2. Results

The efficiency of Compound 1 was assessed using the pΔPSP plasmid containing the HIV-1 proviral genome deleted between nucleotides 1511 and 4550 which recapitulates all splicing events of HIV-1 pre-mRNA in transfected HeLa cells.

The mRNAs produced by splicing were then analysed by RT-PCR using forward and reverse primers that amplify several splicing isoforms encoding the viral proteins Nef, Rev, and Tat. Compound 1 used at a concentration of 5 uM or 10 uM did not alter the splicing profile.

In order to verify that Compound 1 does not significantly affect the splicing events of endogenous genes, which could potentially lead to some adverse effects, the effect of Compound 1 was tested by RT-PCR analysis of global alternative splicing on 382 alternative splicing events. These 382 alternative splicing events (ASEs) represent a high throughput random snapshot of global alterations of alternative splicing. High throughput PCR analysis of these (essentially random) 382 ASEs on multiple PBMC samples was performed, either from untreated (cells) or treated with DMSO, Compound 1 or with the control antiviral drug (Darunavir). Analysis of the data allowed further stringent quality controls; ASEs were only considered if >75% of the products ran at the expected mobilities (i.e. if the reactions were pure) and if total expected PCR concentration was higher than 20 nM (i.e. if the reactions were strong) which led to 264 remaining ASEs.

The splicing profiles of the 12 PBMC samples show that there is very little difference in the splicing profiles of the drug-treated PBMC samples as they form one of three separate poles with the stem cells and their derived fibroblasts. Consistent with this, the untreated cells and Compound 1 treated cells percent spliced in values for these 264 ASEs had a correlation of R=0.89, whereas stem cells and derived fibroblasts only correlated at R=0.59 (data not shown). Taken together these data show that Compound 1 has no global effect on pre-mRNA splicing.

To test whether Compound 1 influences the splicing of HIV RNA in infected cells, an array-based sequence capture was performed using a customized library probes targeting HIV sequences to get rid of cellular RNA. The probes were used to capture cDNAs prepared from infected treated and untreated PBMCs. After double capture, libraries were prepared and sequenced using 454 pyrosequencing (according to GS junior method manual). The average size of the reads around 400 bp allowed unambiguous assembly of viral genome from untreated sample (after 3 and 6 days of infection) using reads that were not mapped to human genome (hg19). All sequencing data were analysed using gsnap, as detailed in Wu et al. (Fast and SNP-tolerant detection of complex variants and splicing in short reads. Bioinformatics 26, 873-881 (2010)).

After 3 days post infection a higher coverage of viral genome for the untreated DMSO sample (32,289 reads) was obtained compared to Compound 1 treated sample (4149 reads). Strikingly, at 3 days post-infection 17.4% of the reads from treated sample corresponded to splice junctions, against 0.93% in the untreated sample. While the number of reads from treated and untreated samples were similar at 6 days post-infection (20 585 and 27 984, respectively), the fraction corresponding to splice junctions was again larger in treated (13.3%) compared to untreated sample (1.93%).

Based on these results it may be concluded that Compound 1 favours spliced HIV RNA in infected PBMCs, thereby compromising subsequent synthesis of full-length HIV-1 pre-mRNA and assembly of infectious particles.

SEQUENCE LISTING

| | | |
|---|---|---|
| SEQ No 1 | Protein Sequence of human CBP20 | |
| | MSGGLLKALRSDSYVELSQYRDQHFRGDNEEQEKLLKK | |
| | SCTLYVGNLSFYTTEEQIYELFSKSGDIKKIIMGLDKM | |
| | KKTACGFCFVEYYSRADAENAMRYINGTRLDDRIIRTD | |
| | WDAGFKEGRQYGRGRSGGQVRDEYRQDYDAGRGGYGKL | |
| | AQNQ | |
| SEQ No 2 | Fragment of human CBP20; from position 38 to 67. | |
| | KSCTLYVGNLSFYTTEEQIYELFSKSGDIK | |
| SEQ No 3 | Protein Sequence of human CBP80 | |
| | MSRRRHSDENDGGQPHKRRKTSDANETEDHLESLICKV | |
| | GEKSACSLESNLEGLAGVLEADLPNYKSKILRLLCTVA | |
| | RLLPEKLTIYTTLVGLLNARNYNFGGEFVEAMIRQLKE | |
| | SLKANNYNEAVYLVRFLSDLVNCHVIAAPSMVAMFENF | |
| | VSVTQEEDVPQVRRDWYVYAFLSSLPWVGKELYEKKDA | |
| | EMDRIFANTESYLKRRQKTHVPMLQVWTADKPHPQEEY | |
| | LDCLWAQIQKLKKDRWQERHILRPYLAFDSILCEALQH | |
| | NLPPFTPPPHTEDSVYPMPRVIFRMFDYTDDPEGPVMP | |
| | GSHSVERFVIEENLHCIIKSHWKERKTCAAQLVSYPGK | |
| | NKIPLNYHIVEVIFAELFQLPAPPHIDVMYTTLLIELC | |
| | KLQPGSLPQVLAQATEMLYMRLDTMNTTCVDRFINWFS | |
| | HHLSNFQFRWSWEDWSDCLSQDPESPKPKFVREVLEKC | |
| | MRLSYHQRILDIVPPTFSALCPANPTCIYKYGDESSNS | |
| | LPGHSVALCLAVAFKSKATNDEIFSILKDVPNPNQDDD | |
| | DDDEGFSFNPLKIEVFVQTLLHLAAKSFSHSFSALAKF | |
| | HEVFKTLAESDEGKLHVLRVMFEVWRNHPQMIAVLVDK | |
| | MIRTQIVDCAAVANWIFSSELSRDFTRLFVWEILHSTI | |
| | RKMNKHVLKIQKELEEAKEKLARQHKRRSDDDDRSSDR | |
| | KGVLEEQIERLQEKVESAQSEQKNLFLVIFQRFIMILT | |
| | EHLVRCETDGTSVLTPWYKNCIERLQQIFLQHHQIIQQ | |
| | YMVTLENLLFTAELDPHILAVFQQFCALQA | |
| SEQ No 4 | Fragment of human CBP20; from position 38 to 119. | |
| | KSCTLYVGNLSFYTTEEQIYELFSKSGDIKKIIMGLDK | |
| | MKTACGFCFVEYYSRADAENAMRYINGTRLDDRIIRTD | |
| | WDAG | |
| SEQ No 5 | DNA sequence corresponding to the Rev Response Element | |
| | GAGAAGAGTGGTGCAGAGAGAAAAAGAGCAGTGGGAA | |
| | TAGGAGCTTTGTTCCTTGGGTTCTTGGGAGCAGCAGGA | |
| | AGCACTATGGGCGCAGCCTCAATGACGCTGACGGTACA | |
| | GGCCAGACAATTATTGTCTGGTATAGTGCAGCAGCAGA | |
| | ACAATTTGCTGAGGGCTATTGAGGCGCAACAGCATCTG | |
| | TTGCAACTCACAGTCTGGGGCATCAAGCAGCTCCAGGC | |
| | AAGAATCCTGGCTGTGGAAAGATACCTAAAGGATCAAC | |
| | AGCTCCTGGGGATTTGGGGTTGCTCTGGAAAACTCATT | |
| | TGCACCACTGCTGTGCCTTGGAATG | |

| SEQ No 6 | DNA nucleic acid encoding the Amino acid sequence of Rev |
|---|---|

ATGGCAGGAAGAAGCGGAGACAGCGACGAAGAGCTCAT
CAGAACAGTCAGACTCATCAAGTTTCTCTATCAAAGCA
ACCCACCTCCCAACCCCGAGGGGACCCGACAGGCCCGA
AGGAATAGAAGAAGAAGGTGGAGAGAGAGACAGAGACA

GATCCATTCGATTAGTGAACGGATCCTTAGCACTTATC
TGGGACGATCTGCGGACGCTGTGCCTCTTCAGCTACCA
CCGCTTGAGAGACTTACTCTTGATTGTAACGAGGATTG
TGGAACTTCTGGGACGCAGGGGTGGGAAGCCCTCAAA
TATTGGTGGAATCTCCTACAGTATTGGAGTCAGGAACT
AAAGAATAG

The invention claimed is:

1. A method for screening a compound useful for treating or reducing the likelihood of occurrence or reoccurrence of a retroviral infection or a retrovirus-related condition in an individual, comprising at least the steps of:
   a) providing a sample, and
   b) contacting the sample with a candidate compound, and measuring an ability of the compound to promote an interaction between Cap-Binding Protein 20 (CBP20) and Cap-Binding Protein 80 (CBP80) in the sample.

2. The method according to claim 1, further comprising a step of determining the ability of the compound to interact with CBP20 in a sample.

3. The method according to claim 1, further comprising a step of determining the ability of the compound to interact with a fragment of CBP20 which binds to CBP80.

4. The method according to claim 3, wherein the fragment of CBP20 includes SEQ ID No 2.

5. The method according to claim 1, further comprising a step of determining an ability of the candidate compound to not interact with the cap binding site of CBP20.

6. The method according to claim 1, further comprising determining an ability of the candidate compound to interact with Rev; and/or to decrease the activity of Rev.

7. The method according to claim 1, wherein CBP20 and/or CBP80 are recombinant polypeptides, synthetic polypeptides, or fragments thereof.

8. The method according to claim 1, wherein the retrovirus is human immunodeficiency virus (HIV).

9. The method according to claim 1, wherein the retrovirus-related condition is acquired immune deficiency syndrome (AIDS).

10. The method according to claim 1, wherein the interaction between CBP20 and CBP80 is determined by at least one technique selected from the group consisting of: limited proteolysis, co-immunoprecipitation, Bimolecular Fluorescence Complementation (BiFC), Fluorescence Resonance Energy Transfer (FRET), Radio-immunoassay, ELISA, Yeast two-Hybrid (Y2H) and Protein-fragment Complementation Assay (PCA), Affinity Electrophoresis or Gel-mobility shift assay, affinity chromatography, pull-down assay, co-immunoprecipitation, phage display, chemical crosslinking, tandem affinity purification (TAP), Microscale Thermophoresis (MST), Surface Plasmon Resonance (SPR), Fluorescence Anisotropy, Isothermal Titration calorimetry (ITC), Mass Spectrometry, X-ray crystallography, Nuclear Magnetic Resonance (NMR), Electron Microscopy and Protein Docking.

11. The method according to claim 1, wherein the candidate compound is of formula:

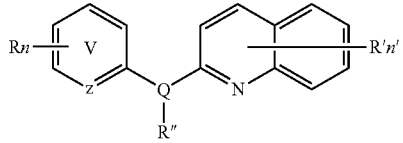

or a pharmaceutically acceptable salt thereof, wherein:

z represents N or C,

means an aromatic ring in which V is C or N, and when V is N, V is in ortho, meta, or para of z, R independently represents a hydrogen atom, a halogen atom or a group chosen among a —CN group, a hydroxyl group, a —COOR$_1$ group, a (C$_1$-C$_3$)fluoroalkyl group, a (C$_1$-C$_3$)fluoroalkoxy group, a (C$_3$-C$_6$)cycloalkyl group, a —NO$_2$ group, a —NR$_1$R$_2$ group, a (C$_1$-C$_4$)alkoxy group, a phenoxy group, a —NR$_1$SO$_2$NR$_1$R$_2$ group, a —NR$_1$SO$_2$R$_1$ group, a —NR$_1$C(=O)R$_1$ group, a —NR$_1$C(=O)—NR$_1$R$_2$ group, a —SO$_2$NR$_1$R$_2$ group, a —SO$_3$H group, a —O—SO$_2$—OR$_3$ group, a —O—P(=O)(OR$_3$)(OR$_4$) group, a —O—CH$_2$—COOR$_3$ group, and a (C$_1$-C$_3$)alkyl group, said alkyl being optionally mono-substituted by a hydroxyl group, Q is N or O, provided that R" does not exist when Q is O, R$_1$ and R$_2$ are independently a hydrogen atom or a (C$_1$-C$_3$)alkyl group, R$_3$ and R$_4$ independently represent a hydrogen atom, Li+, Na+, K+, N+(Ra)$_4$, or a benzyl group, n is 1, 2 or 3, n' is 1, 2 or 3, R' independently represents a hydrogen atom or a group chosen among a (C$_1$-C$_3$)alkyl group, a halogen atom, a hydroxyl group, a —COOR$_1$ group, a —NO$_2$ group, a —NR$_1$R$_2$ group, a morpholinyl or a morpholino group, a N-methylpiperazinyl group, a (C$_1$-C$_3$)fluoroalkyl group, a (C$_1$-C$_4$)alkoxy group, and a —CN group, and can further be a group chosen among:

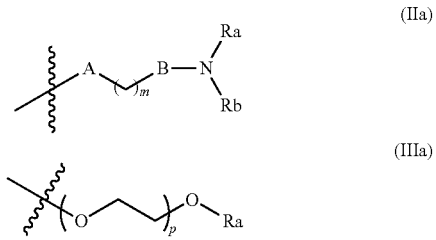

A is a covalent bond, an oxygen atom, or NH,

B is a covalent bond or NH, m is 1, 2, 3, 4 or 5, p is 1, 2 or 3,

Ra and Rb independently represent a hydrogen atom, a (C$_1$-C$_5$)alkyl group or a (C$_3$-C$_6$)cycloalkyl group, Ra and Rb can further form together with the nitrogen atom to which they are attached a saturated 5- or 6-membered heterocycle optionally containing a further heteroatom chosen among N, O, and S, said heterocycle being optionally substituted by one or more Ra, provided that when R' is a group (IIa) or (IIIa), n' may be 2 or 3 only if other R' groups are different from said group (IIa) or (IIIa), R" is a hydrogen atom, a (C$_1$-C$_4$)alkyl group or is a group (IIa) as defined above, or wherein the candidate compound is of formula:

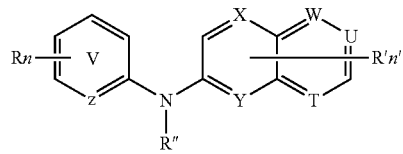

or anyone of its pharmaceutically acceptable salts or anyone of its metabolites, wherein:

means an aromatic ring in which V is C or N, and when V is N, V is in ortho, meta, or para of Z, R independently represents a hydrogen atom, a halogen atom or a group chosen among a —CN group, a hydroxyl group, a —COOR$_1$ group, a (C$_1$-C$_3$)fluoroalkyl group, a (C$_1$-C$_3$)fluoroalkoxy group, a —NO$_2$ group, a —NR$_1$R$_2$ group, a (C$_1$-C$_4$)alkoxy group, a phenoxy group, and a (C$_1$-C$_3$)alkyl group, said alkyl being optionally mono-substituted by a hydroxyl group, R₁ and R₂ are independently a hydrogen atom or a (C₁-C₃)alkyl group, n is 1, 2 or 3, n' is 1 or 2, R' is a hydrogen atom or a group chosen among a (C₁-C₃)alkyl group, a halogen atom, a hydroxyl group, a —COOR₁ group, a —NO₂ group, a —NR₁R₂ group, a morpholinyl or a morpholino group, a N-methylpiperazinyl group, a (C₁-C₃)fluoroalkyl group, a (C₁-C₄)alkoxy group and a —CN group, R" is a hydrogen atom or a (C₁-C₄)alkyl group, Z is N or C, Y is N or C, X is N or C, W is N or C, T is N or C, U is N or C, and wherein at most four of the groups V, T, U, Z, Y, X and W are N, and at least one of the groups T, U, Y, X and W is N.

12. A method for screening a compound useful for treating or reducing the likelihood or occurrence or reoccurrence of a retroviral infection or retrovirus-related condition in an individual, comprising at least the steps of:

a) providing a sample, and b) contacting the sample with a candidate compound and measuring an ability of the compound to interact with Cap-Binding Protein 20 (CBP20) or Cap-Binding Protein 80 (CBP80) in the sample.

13. The method according to claim 12, wherein the ability of the compound to interact with CBP20 in the sample is measured.

14. The method according to claim 12, wherein the ability of the compound to interact with a fragment of CBP20 which binds to CBP80 is measured.

15. The method according to claim 14, wherein the fragment of CBP20 includes SEQ ID No 2.

16. The method according to claim 12, further comprising a step of determining an ability of the candidate compound to not interact with the cap binding site of CBP20.

17. The method according to claim 12, further comprising determining an ability of the candidate compound to interact with Rev; and/or to decrease the activity of Rev.

18. The method according to claim 12, wherein CBP20 and/or CBP80 are recombinant polypeptides, synthetic polypeptides, or fragments thereof.

19. The method according to claim 12, wherein the retrovirus is human immunodeficiency virus (HIV).

20. The method according to claim 12, wherein the retrovirus-related condition is acquired immune deficiency syndrome (AIDS).

21. The method according to claim 12, wherein the interaction between (i) the candidate compound and (ii) CBP20 or CBP80 is determined by at least one technique selected from the group consisting of: limited proteolysis, co-immunoprecipitation, Bimolecular Fluorescence Complementation (BiFC), Fluorescence Resonance Energy Transfer (FRET), Radio-immunoassay, ELISA, Yeast two-Hybrid (Y2H) and Protein-fragment Complementation Assay (PCA), Affinity Electrophoresis or Gel-mobility shift assay, affinity chromatography, pull-down assay, co-immunoprecipitation, phage display, chemical crosslinking, tandem affinity purification (TAP), Microscale Thermophoresis (MST), Surface Plasmon Resonance (SPR), Fluorescence Anisotropy, Isothermal Titration calorimetry (ITC), Mass Spectrometry, X-ray crystallography, Nuclear Magnetic Resonance (NMR), Electron Microscopy, and Protein Docking.

22. The method according to claim 12, wherein the candidate compound is of formula:

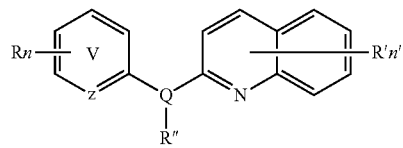

or anyone of its pharmaceutically acceptable salt;

wherein:

z represents N or C,

means an aromatic ring wherein V is C or N and when V is N, V is in ortho, meta or para of z, R independently represents a hydrogen atom, a halogen atom, or a group chosen among a —CN group, a hydroxyl group, a —COOR₁ group, a (C₁-C₃)fluoroalkyl group, a (C₁-C₃)fluoroalkoxy group, a (C₃-C₆)cycloalkyl group, a —NO₂ group, a —NR₁R₂ group, a (C₁-C₄)alkoxy group, a phenoxy group, a —NR₁SO₂NR₁R₂ group, a —NR₁SO₂R₁ group, a —NR₁C(=O)R₁ group, a —NR₁C(=O)—NR₁R₂ group, a —SO₂NR₁R₂ group, a —SO₃H group, a —O—SO₂—OR₃ group, a —OP(=O)(OR₃)(OR₄) group, a —O—CH₂—COOR₃ group, and a (C₁-C₃) alkyl group, said alkyl being optionally mono-substituted by a hydroxyl group, Q is N or O, provided that R" does not exist when Q is O, R₁ and R₂ are independently a hydrogen atom or a (C₁-C₃)alkyl group, R₃ and R₄ independently represent a hydrogen atom, Li+, Na+, K+, N+(Ra)₄, or a benzyl group, n is 1, 2 or 3, n' is 1, 2 or 3, R' independently represent a hydrogen atom or a group chosen among a (C₁-C₃)alkyl group, a halogen atom, a hydroxyl group, a —COOR₁ group, a —NO2 group, a —NR₁R₂ group, a morpholinyl or a morpholino group, a N-methylpiperazinyl group, a (C₁-C₃)fluoroalkyl group, a (C₁-C₄)alkoxy group, and a —CN group, and can further be a group chosen among:

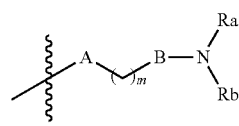

(IIa)

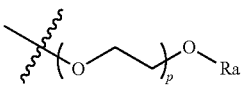

(IIIa)

A is a covalent bond, an oxygen atom or NH,
B is a covalent bond or NH,
m is 1, 2, 3, 4 or 5,
p is 1, 2 or 3,
Ra and Rb independently represent a hydrogen atom, a ($C_1$-$C_5$)alkyl group, or a ($C_3$-$C_6$)cycloalkyl group,
Ra and Rb can further form together with the nitrogen atom to which they are attached a saturated 5- or 6-membered heterocycle optionally containing a further heteroatom chosen among N, O and S, said heterocycle being optionally substituted by one or more Ra, provided that when R' is a group (IIa) or (IIIa), n' may be 2 or 3 only if other R' groups are different from said group (IIa) or (IIIa),
R" is a hydrogen atom, a ($C_1$-$C_4$)alkyl group, or is a group (IIa) as defined above,
or wherein the candidate compound is of formula:

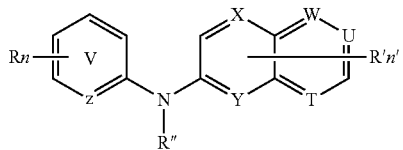

or anyone of its pharmaceutically acceptable salts or anyone of its metabolites,
wherein:

means an aromatic ring wherein V is C or N and when V is N, V is in ortho, meta or para of Z, R independently represents a hydrogen atom, a halogen atom, or a group chosen among a —CN group, a hydroxyl group, a —COOR$_1$ group, a ($C_1$-$C_3$)fluoroalkyl group, a ($C_1$-$C_3$)fluoroalkoxy group, a —NO$_2$ group, a —NR$_1$R$_2$ group, a ($C_1$-$C_4$)alkoxy group, a phenoxy group, and a ($C_1$-$C_3$)alkyl group, said alkyl being optionally mono-substituted by a hydroxyl group,
R$_1$ and R$_2$ are independently a hydrogen atom or a ($C_1$-$C_3$)alkyl group,
n is 1, 2 or 3,
n' is 1 or 2,
R' is a hydrogen atom or a group chosen among a ($C_1$-$C_3$)alkyl group, a halogen atom, a hydroxyl group, a —COOR$_1$ group, a —NO$_2$ group, a —NR$_1$R$_2$ group, a morpholinyl or a morpholino group, a N-methylpiperazinyl group, a ($C_1$-$C_3$)fluoroalkyl group, a ($C_1$-$C_4$) alkoxy group and a —CN group,
R" is a hydrogen atom or a ($C_1$-$C_4$)alkyl group,
Z is N or C,
Y is N or C,
X is N or C,
W is N or C,
T is N or C,
U is N or C,
and wherein at most four of the groups V, T, U, Z, Y, X and W are N,
and at least one of the groups T, U, Y, X and W is N.

23. A method comprising:
performing the method according to claim 1; and
administering the candidate compound to the individual if the candidate compound has the ability to promote the interaction between CPB20 and CBP80.

24. A method comprising:
performing the method according to claim 12; and
administering the candidate compound to the individual if the candidate compound has the ability to interact with CBP20 or CBP80.

* * * * *

SEQUENCE LISTING

<160> NUMBER OF SEQ ID NOS: 6

<210> SEQ ID NO 1
<211> LENGTH: 156
<212> TYPE: PRT
<213> ORGANISM: Homo sapiens
<220> FEATURE:
<223> OTHER INFORMATION: CBP20

<400> SEQUENCE: 1

Met Ser Gly Gly Leu Leu Lys Ala Leu Arg Ser Asp Ser Tyr Val Glu
1               5                   10                  15

Leu Ser Gln Tyr Arg Asp Gln His Phe Arg Gly Asp Asn Glu Glu Gln
            20                  25                  30

Glu Lys Leu Leu Lys Lys Ser Cys Thr Leu Tyr Val Gly Asn Leu Ser
        35                  40                  45

Phe Tyr Thr Thr Glu Glu Gln Ile Tyr Glu Leu Phe Ser Lys Ser Gly
    50                  55                  60

Asp Ile Lys Lys Ile Ile Met Gly Leu Asp Lys Met Lys Lys Thr Ala
65                  70                  75                  80

Cys Gly Phe Cys Phe Val Glu Tyr Tyr Ser Arg Ala Asp Ala Glu Asn
                85                  90                  95

Ala Met Arg Tyr Ile Asn Gly Thr Arg Leu Asp Asp Arg Ile Ile Arg
            100                 105                 110

Thr Asp Trp Asp Ala Gly Phe Lys Glu Gly Arg Gln Tyr Gly Arg Gly
        115                 120                 125

Arg Ser Gly Gly Gln Val Arg Asp Glu Tyr Arg Gln Asp Tyr Asp Ala
    130                 135                 140

Gly Arg Gly Gly Tyr Gly Lys Leu Ala Gln Asn Gln
145                 150                 155

<210> SEQ ID NO 2
<211> LENGTH: 30
<212> TYPE: PRT
<213> ORGANISM: Homo sapiens
<220> FEATURE:
<223> OTHER INFORMATION: CBP20 from position 38 to 67

<400> SEQUENCE: 2

Lys Ser Cys Thr Leu Tyr Val Gly Asn Leu Ser Phe Tyr Thr Thr Glu
1               5                   10                  15

Glu Gln Ile Tyr Glu Leu Phe Ser Lys Ser Gly Asp Ile Lys
            20                  25                  30

<210> SEQ ID NO 3
<211> LENGTH: 790
<212> TYPE: PRT
<213> ORGANISM: Homo sapiens
<220> FEATURE:
<223> OTHER INFORMATION: CBP80

<400> SEQUENCE: 3

```
Met Ser Arg Arg His Ser Asp Glu Asn Asp Gly Gln Pro His
1               5                   10                  15

Lys Arg Arg Lys Thr Ser Asp Ala Asn Glu Thr Glu Asp His Leu Glu
                20                  25                  30

Ser Leu Ile Cys Lys Val Gly Glu Lys Ser Ala Cys Ser Leu Glu Ser
            35                  40                  45

Asn Leu Glu Gly Leu Ala Gly Val Leu Glu Ala Asp Leu Pro Asn Tyr
        50                  55                  60

Lys Ser Lys Ile Leu Arg Leu Leu Cys Thr Val Ala Arg Leu Leu Pro
65                  70                  75                  80

Glu Lys Leu Thr Ile Tyr Thr Thr Leu Val Gly Leu Leu Asn Ala Arg
                85                  90                  95

Asn Tyr Asn Phe Gly Gly Glu Phe Val Glu Ala Met Ile Arg Gln Leu
            100                 105                 110

Lys Glu Ser Leu Lys Ala Asn Asn Tyr Asn Glu Ala Val Tyr Leu Val
            115                 120                 125

Arg Phe Leu Ser Asp Leu Val Asn Cys His Val Ile Ala Ala Pro Ser
        130                 135                 140

Met Val Ala Met Phe Glu Asn Phe Val Ser Val Thr Gln Glu Glu Asp
145                 150                 155                 160

Val Pro Gln Val Arg Arg Asp Trp Tyr Val Tyr Ala Phe Leu Ser Ser
                165                 170                 175

Leu Pro Trp Val Gly Lys Glu Leu Tyr Glu Lys Lys Asp Ala Glu Met
            180                 185                 190

Asp Arg Ile Phe Ala Asn Thr Glu Ser Tyr Leu Lys Arg Arg Gln Lys
        195                 200                 205

Thr His Val Pro Met Leu Gln Val Trp Thr Ala Asp Lys Pro His Pro
        210                 215                 220

Gln Glu Glu Tyr Leu Asp Cys Leu Trp Ala Gln Ile Gln Lys Leu Lys
225                 230                 235                 240

Lys Asp Arg Trp Gln Glu Arg His Ile Leu Arg Pro Tyr Leu Ala Phe
                245                 250                 255

Asp Ser Ile Leu Cys Glu Ala Leu Gln His Asn Leu Pro Pro Phe Thr
            260                 265                 270

Pro Pro Pro His Thr Glu Asp Ser Val Tyr Pro Met Pro Arg Val Ile
        275                 280                 285

Phe Arg Met Phe Asp Tyr Thr Asp Asp Pro Glu Gly Pro Val Met Pro
290                 295                 300

Gly Ser His Ser Val Glu Arg Phe Val Ile Glu Glu Asn Leu His Cys
305                 310                 315                 320

Ile Ile Lys Ser His Trp Lys Glu Arg Lys Thr Cys Ala Ala Gln Leu
                325                 330                 335

Val Ser Tyr Pro Gly Lys Asn Lys Ile Pro Leu Asn Tyr His Ile Val
            340                 345                 350

Glu Val Ile Phe Ala Glu Leu Phe Gln Leu Pro Ala Pro Pro His Ile
        355                 360                 365

Asp Val Met Tyr Thr Thr Leu Leu Ile Glu Leu Cys Lys Leu Gln Pro
        370                 375                 380

Gly Ser Leu Pro Gln Val Leu Ala Gln Ala Thr Glu Met Leu Tyr Met
385                 390                 395                 400

Arg Leu Asp Thr Met Asn Thr Thr Cys Val Asp Arg Phe Ile Asn Trp
                405                 410                 415
```

```
Phe Ser His His Leu Ser Asn Phe Gln Phe Arg Trp Ser Trp Glu Asp
            420                 425                 430
Trp Ser Asp Cys Leu Ser Gln Asp Pro Glu Ser Pro Lys Pro Lys Phe
        435                 440                 445
Val Arg Glu Val Leu Glu Lys Cys Met Arg Leu Ser Tyr His Gln Arg
    450                 455                 460
Ile Leu Asp Ile Val Pro Pro Thr Phe Ser Ala Leu Cys Pro Ala Asn
465                 470                 475                 480
Pro Thr Cys Ile Tyr Lys Tyr Gly Asp Glu Ser Ser Asn Ser Leu Pro
                485                 490                 495
Gly His Ser Val Ala Leu Cys Leu Ala Val Ala Phe Lys Ser Lys Ala
            500                 505                 510
Thr Asn Asp Glu Ile Phe Ser Ile Leu Lys Asp Val Pro Asn Pro Asn
        515                 520                 525
Gln Asp Asp Asp Asp Glu Gly Phe Ser Phe Asn Pro Leu Lys Ile
    530                 535                 540
Glu Val Phe Val Gln Thr Leu Leu His Leu Ala Ala Lys Ser Phe Ser
545                 550                 555                 560
His Ser Phe Ser Ala Leu Ala Lys Phe His Glu Val Phe Lys Thr Leu
                565                 570                 575
Ala Glu Ser Asp Glu Gly Lys Leu His Val Leu Arg Val Met Phe Glu
            580                 585                 590
Val Trp Arg Asn His Pro Gln Met Ile Ala Val Leu Val Asp Lys Met
        595                 600                 605
Ile Arg Thr Gln Ile Val Asp Cys Ala Ala Val Ala Asn Trp Ile Phe
610                 615                 620
Ser Ser Glu Leu Ser Arg Asp Phe Thr Arg Leu Phe Val Trp Glu Ile
625                 630                 635                 640
Leu His Ser Thr Ile Arg Lys Met Asn Lys His Val Leu Lys Ile Gln
                645                 650                 655
Lys Glu Leu Glu Glu Ala Lys Glu Lys Leu Ala Arg Gln His Lys Arg
            660                 665                 670
Arg Ser Asp Asp Asp Asp Arg Ser Ser Asp Arg Lys Asp Gly Val Leu
        675                 680                 685
Glu Glu Gln Ile Glu Arg Leu Gln Glu Lys Val Glu Ser Ala Gln Ser
690                 695                 700
Glu Gln Lys Asn Leu Phe Leu Val Ile Phe Gln Arg Phe Ile Met Ile
705                 710                 715                 720
Leu Thr Glu His Leu Val Arg Cys Glu Thr Asp Gly Thr Ser Val Leu
                725                 730                 735
Thr Pro Trp Tyr Lys Asn Cys Ile Glu Arg Leu Gln Gln Ile Phe Leu
            740                 745                 750
Gln His His Gln Ile Ile Gln Gln Tyr Met Val Thr Leu Glu Asn Leu
        755                 760                 765
Leu Phe Thr Ala Glu Leu Asp Pro His Ile Leu Ala Val Phe Gln Gln
770                 775                 780
Phe Cys Ala Leu Gln Ala
785                 790

<210> SEQ ID NO 4
<211> LENGTH: 80
<212> TYPE: PRT
<213> ORGANISM: Homo sapiens
<220> FEATURE:
<223> OTHER INFORMATION: CBP20 from position 38 to 119
```

```
<400> SEQUENCE: 4

Lys Ser Cys Thr Leu Tyr Val Gly Asn Leu Ser Phe Tyr Thr Thr Glu
1               5                   10                  15

Glu Gln Ile Tyr Glu Leu Phe Ser Lys Ser Gly Asp Ile Lys Lys Ile
            20                  25                  30

Ile Met Gly Leu Asp Lys Met Lys Thr Ala Cys Gly Phe Cys Phe Val
        35                  40                  45

Glu Tyr Tyr Ser Arg Ala Asp Ala Glu Asn Ala Met Arg Tyr Ile Asn
50                      55                  60

Gly Thr Arg Leu Asp Asp Arg Ile Ile Arg Thr Asp Trp Asp Ala Gly
65                  70                  75                  80

<210> SEQ ID NO 5
<211> LENGTH: 329
<212> TYPE: DNA
<213> ORGANISM: Homo sapiens
<220> FEATURE:
<223> OTHER INFORMATION: RRE

<400> SEQUENCE: 5
gagaagagtg gtgcagagag aaaaaagagc agtgggaata ggagctttgt tccttgggtt      60
cttgggagca gcaggaagca ctatgggcgc agcctcaatg acgctgacgg tacaggccag     120
acaattattg tctggtatag tgcagcagca gaacaatttg ctgagggcta ttgaggcgca     180
acagcatctg ttgcaactca cagtctgggg catcaagcag ctccaggcaa gaatcctggc     240
tgtggaaaga tacctaaagg atcaacagct cctggggatt tggggttgct ctggaaaact     300
catttgcacc actgctgtgc cttggaatg                                       329

<210> SEQ ID NO 6
<211> LENGTH: 351
<212> TYPE: DNA
<213> ORGANISM: Homo sapiens
<220> FEATURE:
<223> OTHER INFORMATION: Rev

<400> SEQUENCE: 6
atggcaggaa gaagcggaga cagcgacgaa gagctcatca gaacagtcag actcatcaag      60
tttctctatc aaagcaaccc acctcccaac cccgagggga cccgacaggc ccgaaggaat     120
agaagaagaa ggtggagaga gagacagaga cagatccatt cgattagtga acggatcctt     180
agcacttatc tgggacgatc tgcggacgct gtgcctcttc agctaccacc gcttgagaga     240
cttactcttg attgtaacga ggattgtgga acttctggga cgcaggggt gggaagccct      300 caaatattgg tggaatctcc tacagtattg gagtcaggaa ctaaagaata g              351
```